(12) United States Patent
Srivastava

(10) Patent No.: US 11,126,696 B1
(45) Date of Patent: Sep. 21, 2021

(54) HEALTHCARE RECOMMENDATION AND PREDICTION SYSTEM

(71) Applicant: Evive Health, LLC, Chicago, IL (US)

(72) Inventor: Prashant Srivastava, Chicago, IL (US)

( * ) Notice: Subject to any disclaimer, the term of this patent is extended or adjusted under 35 U.S.C. 154(b) by 621 days.

(21) Appl. No.: 14/752,121

(22) Filed: Jun. 26, 2015

Related U.S. Application Data

(60) Provisional application No. 62/017,392, filed on Jun. 26, 2014.

(51) Int. Cl.
*G16H 50/50* (2018.01)
*G06F 19/00* (2018.01)

(52) U.S. Cl.
CPC .......... *G06F 19/328* (2013.01); *G16H 50/50* (2018.01)

(58) Field of Classification Search
CPC ...................................................... G06Q 50/22
USPC .............................................................. 705/4
See application file for complete search history.

(56) References Cited

U.S. PATENT DOCUMENTS

| | | | | |
|---|---|---|---|---|
| 5,915,241 A * | 6/1999 | Giannini | ............... | G06F 19/328 705/2 |
| 9,129,054 B2 * | 9/2015 | Nawana | ............... | A61B 5/4571 |
| 10,289,804 B2 * | 5/2019 | Chapman | ............... | G06Q 40/02 |
| 2005/0203773 A1 * | 9/2005 | Soto | .................... | G06F 19/3431 705/2 |
| 2006/0149594 A1 * | 7/2006 | Hilligoss | ................ | G16H 40/20 705/2 |
| 2008/0033750 A1 * | 2/2008 | Burriss | .................. | G06Q 50/22 705/2 |
| 2010/0235242 A1 * | 9/2010 | Firminger | .............. | G06Q 30/02 705/14.66 |
| 2012/0004925 A1 * | 1/2012 | Braverman | ............ | G06Q 10/00 705/2 |
| 2012/0239417 A1 * | 9/2012 | Pourfallah | ........... | G06Q 20/102 705/2 |
| 2018/0174043 A1 * | 6/2018 | Po | .......................... | G16H 50/20 |

* cited by examiner

*Primary Examiner* — William E Rankins
(74) *Attorney, Agent, or Firm* — McDonnell Boehnen Hulbert & Berghoff LLP

(57) ABSTRACT

The computer-based systems and methods for healthcare procedure recommendation and prediction disclosed herein include specialized computing components configured with customized software, where the components executing the software are configured to (i) after a patient has scheduled an appointment for a first provider to perform a healthcare procedure, identify and recommend one or more alternative providers having a lower expected out-of-pocket cost than the first provider before the date of the scheduled appointment, and/or (ii) predict a likely follow-up procedure for a scheduled appointment, and provide the predicted follow-up procedure and a recommended provider to perform the predicted follow-up procedure to a patient before (or perhaps during) the scheduled appointment.

17 Claims, 6 Drawing Sheets

HEALTHCARE RECOMMENDATION AND PREDICTION SYSTEM

CROSS-REFERENCE TO RELATED APPLICATIONS

This application claims priority to provisional application 62/017,392 filed on Jun. 26, 2014. The entire contents of the 62/017,392 application are incorporated herein by reference.

BACKGROUND

Unless otherwise indicated herein, the materials described in the background section are not prior art to the claims in this disclosure and are not admitted to be prior art by inclusion in this section.

Typically, when a patient makes a medical appointment (e.g., to visit a physician or specialist, to have a surgery or other medical procedure performed, to have an imaging procedure performed, to have lab tests performed, etc.), the healthcare provider that will be performing medical procedure corresponding to the appointment (e.g., the doctor's office, hospital, clinic, laboratory, etc.) verifies the patient's insurance eligibility electronically.

Currently, individual insurance companies (including the Centers for Medicare and Medicaid Services (CMS)) provide or otherwise interface with a HIPAA Eligibility Transaction System (HETS) and/or other similar systems (such as the Provider Service Center) that allow healthcare providers (e.g., physicians, hospitals, clinics, labs, etc.) and their authorized billing agents to share certain patient medical data for the purposes of preparing accurate insurance claims, determining beneficiary liability, and/or determining whether a particular patient is eligible for a particular procedure.

In the HETS system, when a patient makes an appointment with a healthcare provider for a particular healthcare procedure, the healthcare provider sends a request called a "270 request" message over a secure connection (typically via a clearinghouse/gateway, e.g., Passport, Availity) to the patient's insurance provider. The 270 request message typically includes an indication (e.g., a procedure identifier, "service type" code, or other similar indication) of the type and/or a description of the requested healthcare procedure that will be performed. In addition to a service type code, a 270 request also includes the National Provider Identification (NPID) number of the healthcare provider. Each healthcare provider (i.e., each doctor, hospital, clinic, etc.) in the United States has a unique NPID assigned by the CMS and maintained in an NPI Registry, which is a database of registered healthcare providers. Additionally, many NPIDs in the NPI Registry have an associated "specialty code" that indicates, at least at a high level, the type of healthcare practice (e.g., hospital, MRI clinic, orthopedic practice, etc.) that the healthcare provider is engaged in.

In response to receiving a 270 request message from the healthcare provider, the patient's insurance provider sends a "271 response" message back to the healthcare provider with the requested information, e.g., whether the patient is covered by the insurance company, whether the patient's desired healthcare service is covered by the patient's insurance plan, etc. In other systems, such as the Provider Service Center system for example, providers may inquire as to a particular patient's health insurance coverage by sending electronic messages (messages that are the same as, similar to, or different than the 270/271 messages used by HETS), logging in to a website/portal to submit inquiries and receive responses, placing a phone call, or sending a fax to the Provider Service Center. And in response to the provider's inquiry, the Provider Service Center may respond with one or more electronic messages (including messages received via a website/portal), phone calls, or faxes. Regardless of the method of inquiry or response, the HETS, Provider Service Center, and/or other similar system maintains records of the particular provider inquiries and responses thereto.

SUMMARY

One of the many drawbacks of the existing system where patients schedule appointments with a provider, and where providers verify the patient's insurance coverage with the patient's insurer, is that patients typically have no idea how much a procedure will cost before the provider performs the procedure. Indeed, patients typically do not learn the cost of a particular procedure until they receive an invoice from the healthcare provider after the healthcare provider has performed the procedure.

Even if a patient asks the provider how much a particular procedure will cost when making the appointment, the individual scheduling appointments at the provider typically has no knowledge of how much certain procedures cost because that individual is in charge of making appointments—not estimating costs. In most instances, the appointment scheduler may rarely if ever see actual invoices. But even billing personnel likely cannot tell a particular patient how much a particular procedure will cost the patient because provider typically charges different patients very different prices for the same procedure based on whether the provider accepts the patient's insurance plan, whether the provider is "in-network" or "out-of-network" even if the provider accepts the patient's insurance plan, whether the patient's insurance plan covers the particular procedure at that particular provider, whether the patient's insurer has negotiated any special rates with the provider, whether the patient's insurer has negotiated any other standard discounts with the provider, the patient's co-pay (if applicable), the amount that the patient may have already paid towards his or her annual deductible (if applicable), and possibly other factors.

After the provider has performed the procedure, it is not uncommon for many weeks or months to pass while the provider (i) bills the patient's insurer, (ii) receives reimbursement from the patient's insurer according to the patient's insurance plan, and (iii) finally sends a bill to the patient for any amount remaining. It is often not until after the patient receives an unexpectedly large bill from the provider for performing the procedure that the patient may learn that he or she could have had the procedure performed by a different provider at a much lower out-of-pocket cost based on the patient's specific insurance plan. But at that point, it is too late because the procedure is done and the provider has sent the patient the bill.

One way to overcome or at least ameliorate the above-described drawbacks is to implement a system that is configured to (i) after a patient has scheduled an appointment for a first provider to perform a healthcare procedure, identify and recommend (before the date of the scheduled appointment) one or more alternative providers having a lower expected out-of-pocket cost than the first provider, and/or (ii) predict a likely follow-up procedure for a scheduled appointment, and provide the predicted follow-up procedure and a recommended provider to perform the predicted follow-up procedure to a patient before (or perhaps

DETAILED DESCRIPTION

The disclosed systems and methods are described herein with reference to the figures. It should be understood, however, that numerous variations from the depicted arrangements and functions are possible while remaining within the scope and spirit of the claims. For example, one or more elements may be added, removed, combined, distributed, substituted, re-positioned, re-ordered, and/or otherwise changed. Further, where this description refers to one or more functions being implemented on and/or by one or more devices, one or more machines, and/or one or more networks, it should be understood that one or more of such entities could carry out one or more of such functions by themselves or in cooperation, and may do so by application of any suitable combination of hardware, firmware, and/or software. For example, one or more processors may execute one or more sets of programing instructions and/or computer algorithms as at least part of carrying out of one or more of the functions described herein.

Figure 1:
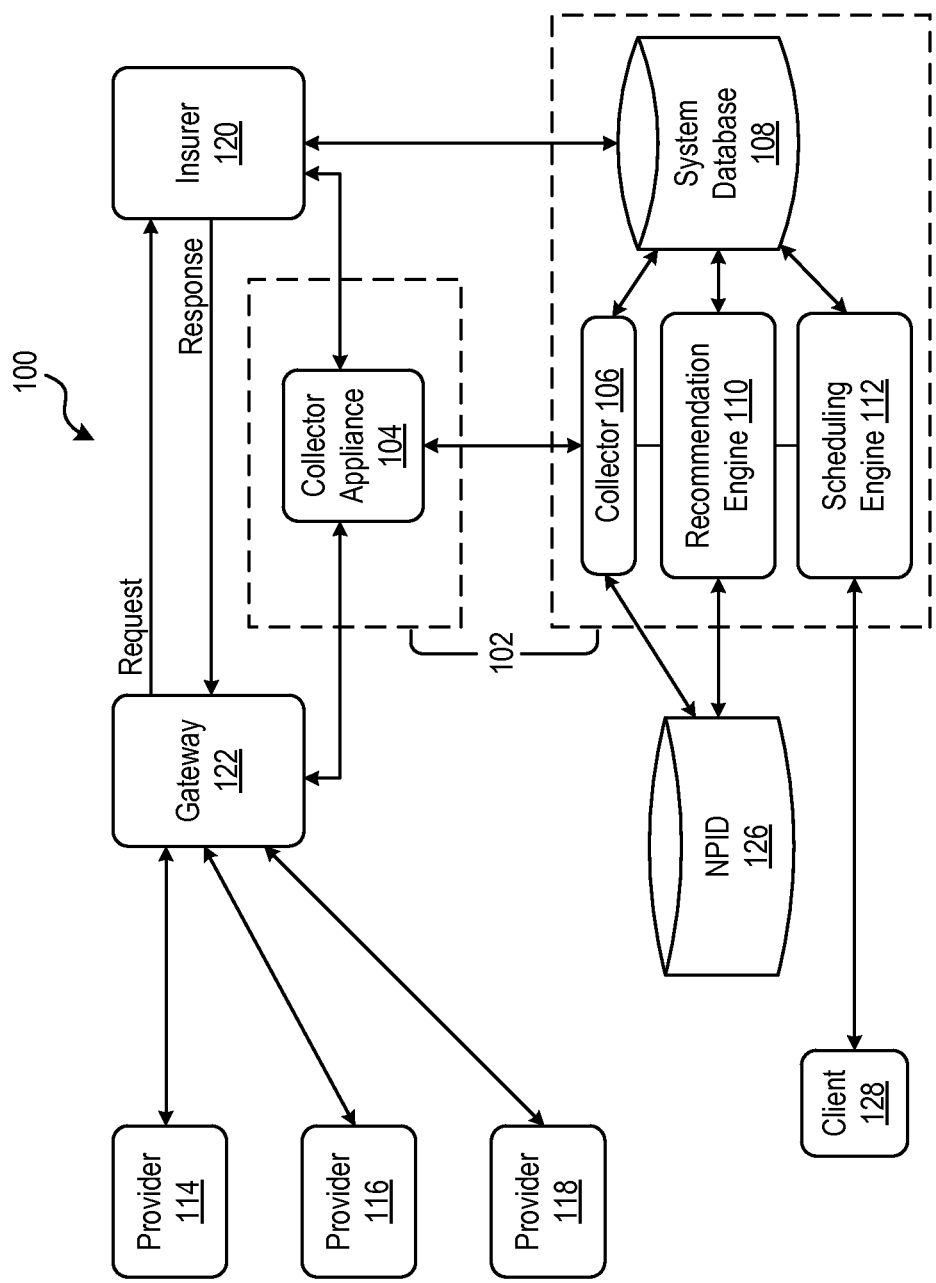
FIG. 1 shows an example healthcare data processing system according to some embodiments of the disclosed systems and methods.

FIG. 1 shows an example healthcare data processing system 102 connected in a network 100 comprising a plurality of healthcare service providers 114-118, a gateway 122, and an insurer 120 according to some embodiments of the disclosed systems and methods. The healthcare data processing system 102 includes a collector appliance 104, a collector 106, a recommendation engine 110, a scheduling engine 112, and a system database 108. The network 100 in FIG. 1 shows a single gateway 122 and a single insurer 120, but the healthcare data processing system 102 may connect to multiple gateways and multiple insurers.

In operation, the system 102 is configured to use information contained in messages exchanged between providers and insurers to recommend healthcare providers for performing specific healthcare procedures, predict follow-up healthcare procedures, and recommend healthcare providers to perform predicted follow-up healthcare procedures.

The one or more provider-insurer messages comprise a patient identifier, a medical procedure identifier, a provider identifier, and a date of service. The provider-insurer messaging corresponds to a particular medical procedure that a particular healthcare provider intends to perform on a particular patient on a particular date. The patient identifier identifies the patient for whom the provider intends to perform the medical procedure, the medical procedure identifier identifies the medical procedure that the provider intends to perform on the patient, the provider identifier identifies the particular healthcare provider that intends to perform the medical procedure, and the date of service identifies the date on which the healthcare provider intends to perform the medical procedure.

In some embodiments, the provider-insurer messaging includes HIPAA Eligibility Transaction System (HETS) messaging, including any of (i) a 270 request from a provider to an insurer, (ii) a 271 response from the insurer to the provider, (iii) a 278 request from a provider to an insurer, and/or (iv) a 278 response message from the insurer to the provider. However, the provider-insurer messaging may take other forms as well, including provider request and insurer response messages other than the specific HIPAA HETS messaging.

The collector appliance 104 is configured to obtain copies of the above-described provider-insurer messages. In particular, the collector application is configured to obtain copies of request messages sent from a provider (e.g., providers 114, 116, and 118) to an insurer (e.g., insurer 120) and/or response messages sent from an insurer (e.g., insurer 120) to a provider (e.g., providers 114, 116, and 118). In some, the collector appliance 104 may is a physical computing device containing a field programmable gate array (FPGA) specifically configured to perform at least some of the functions of the collector appliance described herein. In other embodiments, the collector appliance 104 may be a virtual appliance configured to run highly customized software code that, when executed by the collector appliance 104, cause the collector appliance 104 to perform at least some of the collector appliance functions described herein.

In some embodiments, the collector appliance 104 is co-located with gateway 122. In operation, many providers may connect to a single gateway (e.g., Passport, Availity), which in turn connects to many insurers. This arrangement enables multiple providers to connect with multiple insurers, where the insurers only need to manage a single connection with the gateway so that a provider can connect (and exchange provider-insurer messaging with) multiple insurers but not have to manage multiple provider-insurer connections.

In embodiments, where the collector appliance 104 is co-located with a gateway, the gateway 122 may be configured to send copies of (i) provider-to-insurer messages (e.g., 270 requests) to the collector appliance 104 and/or (ii) insurer-to-provider messages (e.g., 271 responses). In operation, the collector appliance 104 will encrypt the copies of the provider-insurer messages using the public key of system 102, and the collector 106 will decrypt the copies of the provider-insurer messages using the private key of system 102.

Before the collector appliance 104 has encrypted a received provider-insurer message, the collector appliance filters the content of the message based on pre-configured criteria, including but not limited to any combination of one or more of the patient identifier, the group identifier associated with the patient (i.e., the patient's insurance group, which typically corresponds to the patient's employer), the insurer identifier, the procedure identifier, the provider identifier, or perhaps other information in the message to determine whether the system 102 should act on the message. For example, the system 102 may be configured to act only on messages that are associated with one or more particular insurers or groups (e.g., corresponding to an employer health plan for example) or only on particular types of messages (270 for example).

In some embodiments, if the message is a 270 request, and if the collector appliance 104 does not receive a corresponding 271 response within a threshold timeframe to send on to the collector 106, then the collector 106 can send a copy of the 270 request to the insurer 120 to cause the insurer 120 to generate and send a 271 response, which the insurer 120 may send directly to the collector 106.

To send the copy of the 270 request to the insurer 120, the collector 106 encrypts the copy of the 270 request using the public key of the insurer 120. When the insurer 120 receives the encrypted copy of the 270 request, the insurer 120 will decrypt the message with the private key of the insurer 120. Before the insurer 120 sends the 271 response to the collector 106, the insurer 120 will encrypt the 271 response with the public key of the system 102, and when the collector receives the encrypted 271 response from the insurer 120, the collector will decrypt the 271 response with the private key of the system 102.

In other embodiments, the collector appliance 104 may be co-located at the insurer 120. In embodiments where the collector appliance 104 is co-located at the insurer 120, the insurer 120 may be configured to send copies of (i) provider-to-insurer messages (e.g., 270 requests) to the collector appliance 104 and/or (ii) insurer-to-provider messages (e.g., 271 responses). In operation, the collector appliance 104 will encrypt the copies of the provider-insurer messages using the public key of system 102, and the collector 106 will decrypt the copies of the provider-insurer messages using the private key of system 102.

Before the collector appliance 104 has encrypted a received provider-insurer message, the collector appliance filters the content of the message based on pre-configured criteria, including but not limited to any combination of one or more of the patient identifier, the group identifier associated with the patient (i.e., the patient's insurance group, which typically corresponds to the patient's employer), the insurer identifier, the procedure identifier, the provider identifier, or perhaps other information in the message to determine whether the system 102 should act on the message. For example, the system 102 may be configured to act only on messages that are associated with one or more particular insurers or groups (e.g., corresponding to an employer health plan for example).

In some embodiments, if the message is a 270 request, and if the collector appliance 104 does not receive a corresponding 271 response within a threshold timeframe to send on to the collector 106 (i.e., the collector 106 does not receive a 271 response corresponding to the earlier 270 request), the collector 106 can send a copy of the 270 request to the insurer 120 to cause the insurer 120 to generate and send a 271 response, which the insurer 120 will send directly to the collector 106.

To send the copy of the 270 request to the insurer 120, the collector 106 encrypts the copy of the 270 request using the public key of the insurer 120. When the insurer receives the encrypted copy of the 270 request, the insurer 120 decrypts the message using the private key of the insurer 120. When the insurer 120 sends the 271 response to the collector 106 in response to the collector appliance 104 sending the 270 request to the insurer 120, the insurer 120 will encrypt the 271 response with the public key of the system 102, and the collector 106 will decrypt the 271 response with the private key of the system 102.

Once the collector appliance has a 270 request or 271 response (or similar message) on which the system will take action, the collector appliance 104 transmits the 270 request or 271 response (or similar message) to the collector 106 over a secure link using TLS/SSL or a similar security protocol.

The collector 106 is configured to receive messages from the collector appliance 104 over a secure link. In operation, the system may have many collector appliances co-located at multiple gateways and multiple insurers, and the collector 106 is configured to receive messages from the many collector appliances deployed throughout the network at gateway and insurer sites.

When the collector 106 receives a message from the collector appliance 104, the collector 106 decrypts the message using the private key of system 102 and decodes (if necessary) the message, disassembles the message envelope, and extracts the relevant identifiers from the message. For example, in some embodiments, the collector 106 is configured to extract at least the patient identifier, the provider identifier, procedure identifier, and date of service from the message. In other embodiments, the collector 106 may extract more or fewer identifiers from the message.

After extracting the identifiers, the collector 106 uses the patient identifier to access the the system database 108 to retrieve patient profile information, including but not limited to patient data such as (i) patient demographic data (e.g., age, gender, ethnicity, national origin, occupation, education, income, address, family status, and/or other demographic data), (ii) patient health data (e.g., known diseases, allergies, current medications, past medications, doctor visit history, family history of disease, prior injuries/treatments, and/or other health data), and/or (iii) perhaps other patient information. In embodiments, the system database 108 obtains information to populate the patient profile from the patient, the provider, and/or the insurer. In operation, the system database 108 is configured to store and access data stored therein using one or more database applications such as, for example (i) MySQL, NOSQL instances such as Cassandra, Neo4J), (ii) an operating system file system, (ii) Hadoop Distributed File System (HDFS), Spark, Amazon S3, and/or (iv) perhaps other database applications.

The collector 106 also uses the provider identifier to access the system database 108 to obtain provider data. The provider data includes the first provider's specialty, the follow-up procedures that the first provider has prescribed in the past, and/or other data about the first provider. In operation, the system database 108 obtains the provider data from the provider, the National Provider Identification Registry (NPID) 126, Publicly available database such as CMS and/or the insurer.

The collector 106 also uses the procedure identifier to access the system database 108

After the collector 106 retrieves the patient profile information and the provider data from the system database 108, the collector 106 sends the at least some of the retrieved patient profile information and provider data to the recommendation engine 110.

The recommendation engine 110 uses the patient profile information and provider data retrieved by the collector 106 from the system database 108 to recommend providers for performing specific healthcare procedures, predict follow-up healthcare procedures, and recommend healthcare providers to perform predicted follow-up healthcare procedures.

For example, and as described in more detail with reference to FIG. 5, if the date of service for a first provider to perform a procedure for a patient is sufficiently far into the future such that the patient has a reasonable amount of time to reschedule the procedure with an alternative provider (e.g., at least 1-2 days in advance), then the recommendation engine 110 (i) determines the expected patent out-of-pocket cost for the first provider to perform the procedure, and then (ii) identifies and selects a second provider (the alternative provider) that (ii-a) is located within a threshold geographic distance of the first provider (or perhaps within a threshold geographic distance of the patient) and (ii-b) has an expected patient out-of-pocket cost to perform the procedure that is less than the expected patient out-of-pocket cost for the first provider to perform the procedure.

In some embodiments, the recommendation engine 110 may also select the second provider based on whether the second provider (i) has a patient rating that is above a threshold patient rating and/or (ii) is available to perform the procedure within a threshold timeframe of the date of service for the first provider to perform the procedure. As used herein, a patient rating refers to a rating (or score) that a patient has given a particular provider after that provider has performed a particular procedure for the patient. For example, the rating may correspond to patient feedback collected by the system 102 from patients regarding the professionalism of the doctor(s)/staff at the provider, the ease of making an appointment, the quality of care, the condition of the facilities, and/or perhaps other factors.

Once the recommendation engine 110 has selected the second provider, the recommendation engine 110 sends at least the patient identifier, procedure identifier, first provider identifier, expected out-of-pocket cost for the first provider to perform the procedure, the second identifier, the expected out-of-pocket cost for the second provider to perform the procedure to the scheduling engine 112. In some embodiments, the recommendation engine 110 may also send patient ratings for the first and second providers to the scheduling engine 112 too.

Figure 4C:
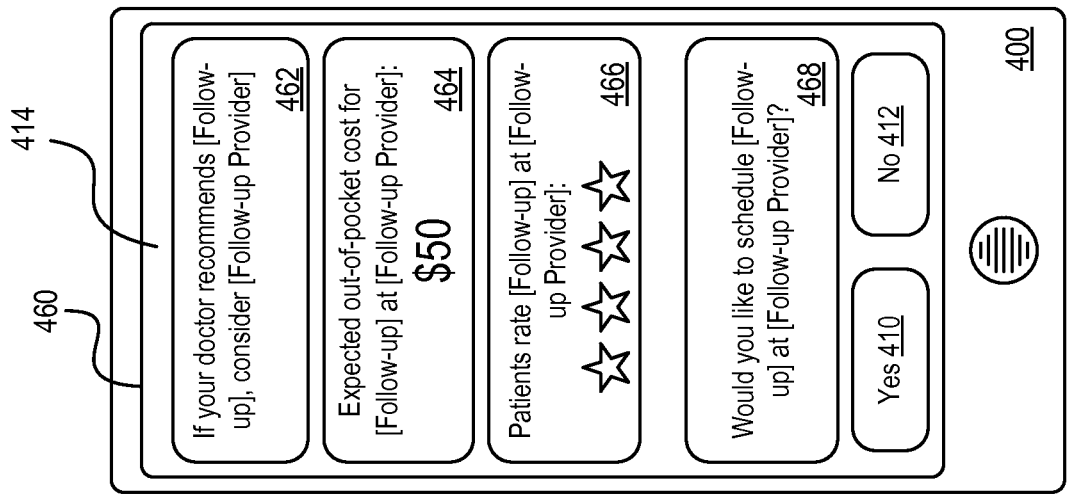
FIG. 4C shows components of another example recommendation displayed within a graphical user interface of a client computing device according to some embodiments of the disclosed systems and methods.
Figure 4B:
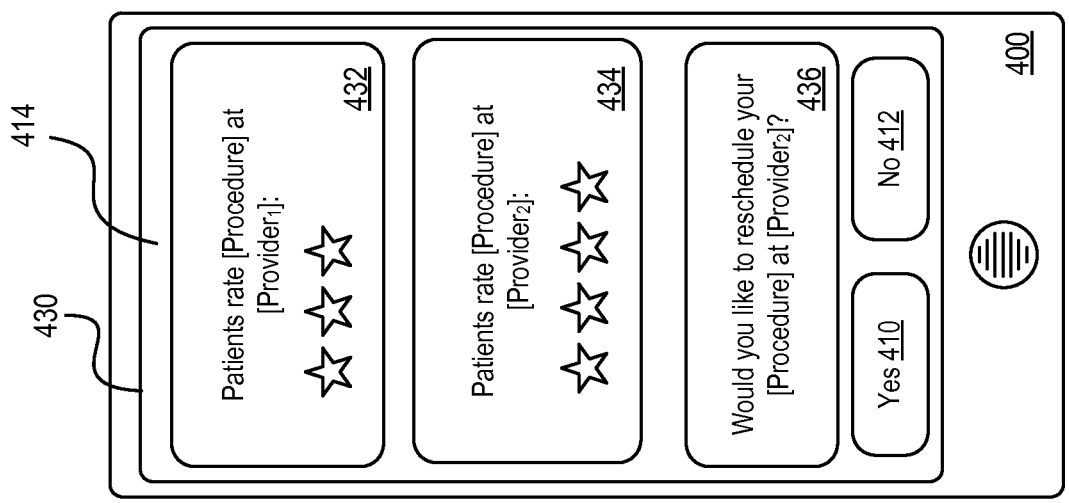
FIG. 4B shows components of another example recommendation displayed within a graphical user interface of a client computing device according to some embodiments of the disclosed systems and methods.
Figure 4A:
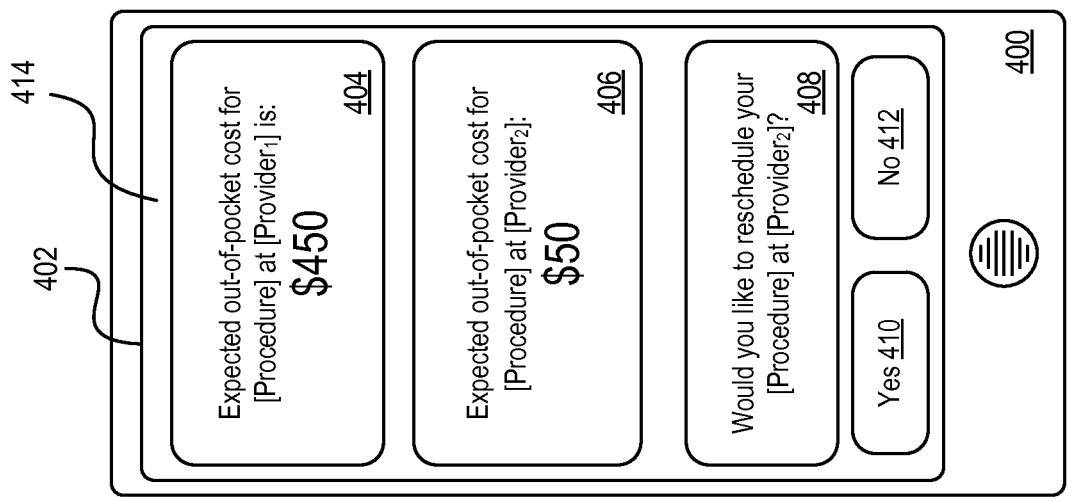
FIG. 4A shows components of an example recommendation displayed within a graphical user interface of a client computing device according to some embodiments of the disclosed systems and methods.

The scheduling engine 112 creates and sends one or more messages to the patient's client device (e.g., client device 128), which in turn displays the messages (or the contents thereof) to the patient. In operation, the one or more messages (individually or in combination) include one or more of the patient identifier, procedure identifier, first provider identifier, expected out-of-pocket cost for the first provider to perform the procedure, the second identifier, the expected out-of-pocket cost for the second provider to perform the procedure, the patient rating for the first provider, and the patient rating for the second provider. In operation, the one or more messages may comprise an email, a letter, a text message, an automated phone call/voicemail message, and/or a message or prompt in a smartphone or tablet-based application. For example, FIGS. 4A-B show example recommendations that a patient's client device 128 displays within a smartphone or tablet-based application in response to receiving the above-described one or more messages from the scheduling engine 112.

The client device 128 may be any type of computing device, such as a desktop or laptop computer, a smartphone, a tablet computer, or other personal computing device. In operation, the patient can choose to schedule the procedure with the second provider (and cancel the procedure with the first provider).

If the patient indicates his or her desire to schedule the procedure with the second provider via one or more inputs on the client device 128, the client device can signal the patient's desire to schedule the procedure with the second provider to the scheduling engine 112. And in response thereto, the scheduling engine 112 sends the client device 128 information for scheduling the procedure with the second provider, e.g., the phone number and/or address of the second provider, a link to the second providers online scheduling interface (if applicable), or other similar information.

In some embodiments, if the patient indicates that he or she does not wish to schedule the procedure with the second provider, and if the patient indicates that desire via one or more inputs on the client device 128, the client device then signals the patient's desire to not schedule the procedure with the second provider to the scheduling engine 112. In response thereto, the system 102 may determine that the patient will simply proceed with the originally-scheduled appointment and have first provider perform the procedure. After the appointment date, the scheduling engine 112 then sends a patient survey to the patient to obtain patient rating information on the procedure and the first provider.

In other embodiments, if the patient indicates that he or she does not wish to schedule the procedure with the second provider, and if the patient indicates that desire via one or more inputs on the client device 128, the client device then signals the patient's desire to not schedule the procedure with the second provider to the scheduling engine 112. In response thereto, the recommendation engine 110 may instead propose an additional alternative provider. The scheduling engine 112 then sends additional messaging with details regarding the additional alternative, expected out-of-pocket cost, and so on as described above. In operation, the system 102 may send the patient's client device 128 multiple additional providers in some instances.

In another example, and as described in more detail with reference to FIG. 5, if the date of service for a first provider to perform a procedure for a patient is not sufficiently far into the future such that the patient has a reasonable amount of time to reschedule the procedure with an alternative provider (e.g., same-day appointment), then the recommendation engine 110 may, in some embodiments, determine whether the first provider is likely to recommend or prescribe a follow-up procedure. And if the recommendation engine 110 determines that the first provider is likely to recommend or prescribe a follow-up procedure, the recommendation engine 110 will predict the most-likely follow-up procedure based at least in part on (i) the procedure that the first provider will perform (or is performing), (ii) patient data such as patient demographic data (e.g., age, gender, ethnicity, national origin, occupation, education, income, address, family status, and/or other demographic data), patient health data (e.g., known diseases, allergies, current medications, past medications, doctor visit history, family history of disease, prior injuries/treatments, and/or other health data), and/or perhaps other patient information, and (iii) the first provider data such as the first provider's specialty, the follow-up procedures that the first provider has prescribed in the past, and/or other data about the first provider.

The recommendation engine 110 performs a Multinomial Logistic Regression Analysis (or similar statistical analysis), where (i) the predictor variables include the procedure, the above-describe patient data, and the above-described first provider data, and (ii) the response variables are a set of potential follow-up procedures. The result of the Multinomial Logistic Regression is a set of probabilities for the set of potential follow-up procedures (one probability for each potential follow-up procedure), where a particular potential follow-up procedure's calculated probability is the probability that the first provider will recommend or prescribe that particular potential follow-up procedure for the patient during the procedure. The recommendation engine 106 selects a follow-up procedure from the set of potential follow-up procedures—typically the procedure with the highest probability of being prescribed by the first provider for the patient during the procedure.

Once the recommendation engine 110 has selected a follow-up procedure (i.e., the predicted follow-up procedure), the recommendation engine 110 then determines one or more providers that can perform the follow-up procedure (i.e., potential follow-up providers) that are within a threshold geographic distance from the first provider (or perhaps from the patient's home or work address). The recommendation engine 110 then ranks the potential follow-up providers based on one or more of (i) expected patient out-of-pocket cost to perform the predicted follow-up procedure, (ii) patient rating, and/or (iii) availability (schedule availability) to perform the predicted follow-up procedure. The recommendation engine 110 then selects the highest ranked potential follow-up provider as the proposed follow-up provider, and sends at least the predicted follow-up procedure, the proposed follow-up provider, the expected out-of-pocket cost for the proposed follow-up provider to perform the predicted follow-up procedure, and the patient rating for the proposed follow-up provider to the scheduling engine 112.

The scheduling engine 112 in turn creates and sends one or more messages to the patient's client device (e.g., client device 128), which in turn displays the messages (or the contents thereof) to the patient. In operation, the one or more messages (individually or in combination) comprise one or more of the patient identifier, predicted follow-up procedure identifier, proposed follow-up provider, the expected out-of-pocket cost for the prosed follow-up provider to perform the predicted follow-up procedure, and the patient rating for the proposed follow-up provider. In operation, the one or more messages may include an email, a letter, a text message, an automated phone call/voicemail message, and/or a message or prompt in a smartphone or tablet-based application. For example, FIG. 4C shows an example recommendations that a patient's client device 128 displays within a smartphone or tablet-based application in response to receiving the above-described one or more messages from the scheduling engine 112.

If the patient indicates his or her desire to schedule the predicted follow-up procedure with the proposed follow-up provider via one or more inputs on the client device 128, the client device signals the patient's desire to schedule the predicted follow-up procedure with the proposed follow-up provider to the scheduling engine 112. And in response thereto, the scheduling engine 112 sends the client device 128 information for scheduling the predicted follow-up procedure with the proposed follow-up provider, e.g., the phone number and/or address of the follow-up provider, a link to the follow-up provider's online scheduling interface (if applicable), or other similar information.

In some embodiments, if the patient indicates that he or she does not wish to schedule the predicted follow-up procedure with the proposed follow-up provider, and if the patient indicates that desire via one or more inputs on the client device 128, the client device then signals the patient's desire to not schedule the predicted follow-up procedure with the proposed follow-up provider to the scheduling engine 112. In response thereto, the system 102 may determine that the first provider did not recommend or prescribe a follow-up procedure. After the appointment date, the scheduling engine 112 then sends a patient survey to the patient to obtain patient rating information on the procedure and the first provider.

In other embodiments, if the patient indicates that he or she does not wish to schedule the predicted follow-up procedure with the proposed follow-up provider, and if the patient indicates that desire via one or more inputs on the client device 128, the client device then signals the patient's desire to not schedule the predicted follow-up procedure with the proposed follow-up provider to the scheduling engine 112. In response thereto, the recommendation engine 110 may then (i) predict another follow-up procedure and/or (ii) propose another follow-up provider. The scheduling engine 112 then sends additional messaging with details regarding the new predicted follow-up procedure and/or new proposed follow-up provider, expected out-of-pocket cost, and so on as described above. In operation, the system 102 may send the patient's client device 128 subsequent predicted follow-up procedures and/or subsequent proposed follow-up providers multiple times in some instances.

Example Recommendation Engine Architecture

The recommendation engine 200 includes one or more processors 202, one or more communication interfaces 204, and data storage 208 configured to store computer readable instructions 210 for execution by the one or more processors 202, all of which are communicatively coupled to each other via a system bus, network, or other connection mechanism 212. In some embodiments, the recommendation engine 200 may also include one or more user interfaces 206. In operation, the recommendation engine 200 is specifically configured to interface with at least one or more collectors, collector appliances, a scheduling engine, and a system database, and the recommendation engine 200 is specifically configured to perform the functions disclosed and described herein. In some embodiments, the recommendation engine 200 may additionally be configured to interface with other networks, such as the Internet and private data networks.

The one or more processors 202 may include one or more general purpose processors (e.g., microprocessors manufactured by Intel or Advanced Micro Devices) and/or one or more special purpose processors (e.g., digital signal processors, application specific integrated circuits, etc.). In operation, the one or more processors 202 are configured to execute the computer-readable program instructions 210 that are contained in the data storage 208 and/or other instructions as described herein.

The one or more communications interfaces 204 may include one or more wireless interfaces and/or wireline interfaces that are configured to communicate with other network computing devices, including but not limited to, for example, other healthcare data processing system components (e.g., collector appliance 104, scheduling engine 112, and system database 108 of healthcare data processing system 102 in FIG. 1), third party databases (e.g., NPID 126 in FIG. 1), other computing systems (e.g., the computing systems of providers 114-118 and the computing systems of insurer 120 in FIG. 1), and client devices (e.g., client device 128 shown and described with reference to FIG. 1). In operation, the one or more communication interfaces 204 may include one or more wireline transceivers, such as Ethernet transceiver(s), Universal Serial Bus (USB) transceiver(s), or similar transceiver(s) configurable to communicate via a twisted pair wire, a coaxial cable, a fiber-optic link or a other type of physical connection to a wireline network. The one or more communication interfaces 204 may additionally or alternatively include one or more wireless transceivers, such as Bluetooth transceiver(s), Wi-Fi transceiver(s), WiMAX transceiver(s), and/or other types of wireless transceivers configurable to communicate via a wireless network.

In some embodiments, the communication interfaces 204 may be configured to provide reliable, secured, and/or authenticated communications. For each communication originating, terminating, or transiting the recommendation engine 200 described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms may be used as well or in addition to those listed herein to secure (and then decrypt/decode) provider-insurer messaging.

The data storage 208 includes one or more computer-readable storage media that can be read and/or written to by at least one of the processors 202. The one or more computer-readable storage media may include volatile and/or non-volatile storage components, such as optical, magnetic, organic or other memory or disc storage, which can be integrated in whole or in part with at least one of the processors 202. In some embodiments, the data storage 208 may be implemented using a single physical device (e.g., one optical, magnetic, organic or other memory or disc storage unit), while in other embodiments, the data storage 208 may be implemented using two or more physical devices.

The data storage 208 includes computer-readable program instructions 210 and perhaps additional data. In some embodiments, the data storage 208 may additionally include storage required to perform at least part of the herein-described techniques and/or at least part of the functionality of the herein-described systems and methods, including but not limited to the features and functions performed by a recommendation engine as disclosed and described herein.

The optional user interfaces 206 are operable to send data to and/or receive data from external user input/output devices. For example, the user interfaces 206 may be configured to send/receive data to/from user input devices such as a keyboard, a keypad, a touch screen, a computer mouse, a track ball, a joystick, and/or other similar devices, now known or later developed. The user interfaces 206 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interfaces 206 may also be configured to generate audible output(s), such as a speaker, speaker jack, audio output port, audio output device, earphones, and/or other similar devices, now known or later developed.

Example Scheduling Engine Architecture

Figure 2A:
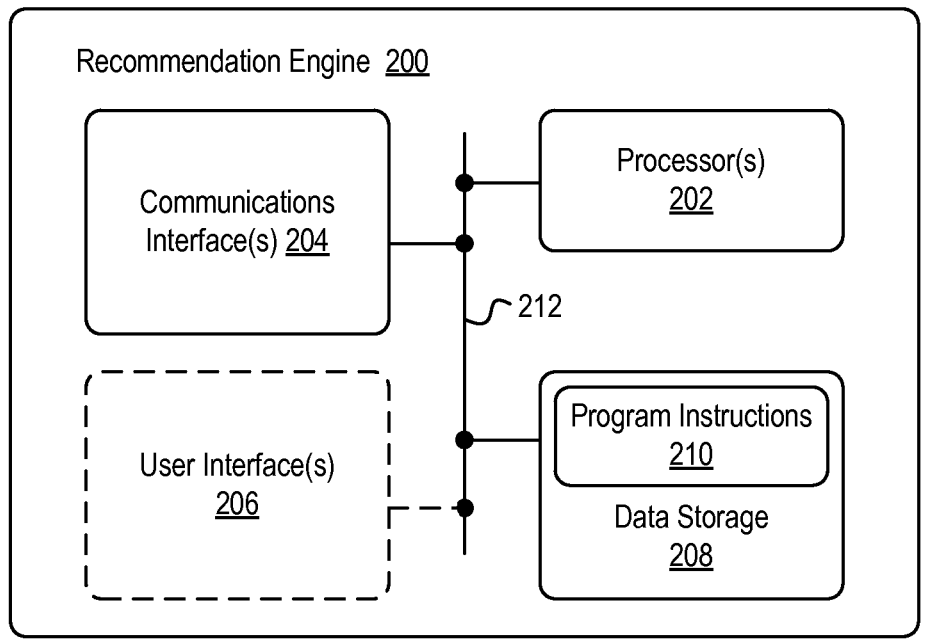
FIG. 2A shows a block diagram of an example recommendation engine according to some embodiments of the disclosed systems and methods.
Figure 2B:
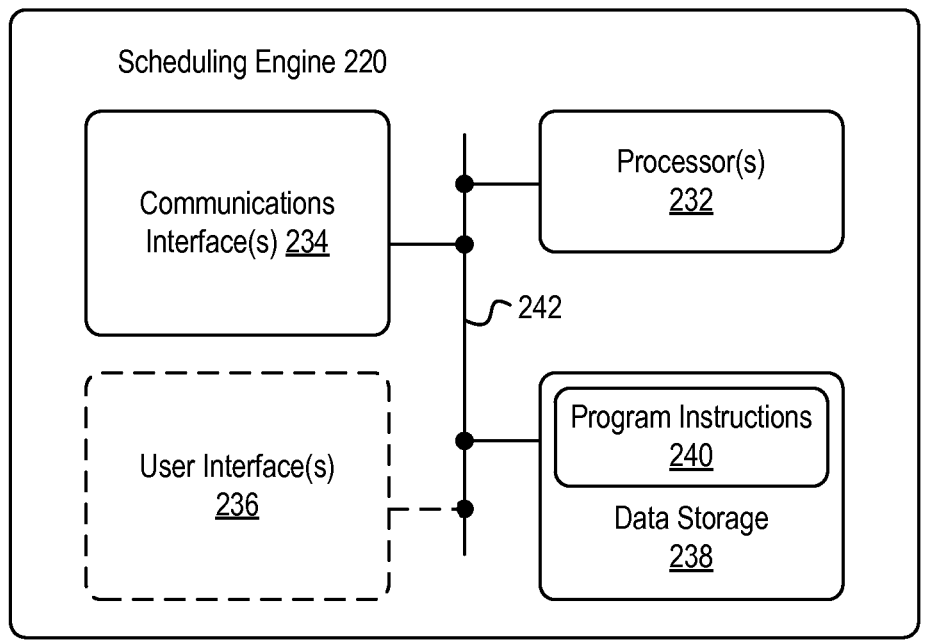
FIG. 2B shows a block diagram of an example scheduling engine according to some embodiments of the disclosed systems and methods.

FIG. 2B shows a block diagram of an example scheduling engine 220 according to some embodiments of the disclosed systems and methods. The example scheduling engine 220 may be similar to or the same as (and may perform the same or similar functions as) any of the scheduling engines described herein, including but not limited to the scheduling engine 112 shown and described with reference to FIG. 1. In operation, the scheduling engine 220 is specifically configured to interface with at least a recommendation engine and one or more client devices, and the scheduling engine 220 is specifically configured to perform the functions disclosed and described herein.

The scheduling engine 230 includes one or more processors 232, one or more communication interfaces 234, and data storage 238 configured to store computer readable instructions 240 for execution by the one or more processors 232, all of which are communicatively coupled to each other via a system bus, network, or other connection mechanism 242. In some embodiments, the scheduling engine 230 may also include one or more user interfaces 236.

The one or more processors 232 may include one or more general purpose processors (e.g., microprocessors manufactured by Intel or Advanced Micro Devices) and/or one or more special purpose processors (e.g., digital signal processors, application specific integrated circuits, etc.). In operation, the one or more processors 232 are configured to execute the computer-readable program instructions 240 that are contained in the data storage 238 and/or other instructions as described herein.

The one or more communications interfaces 234 may include one or more wireless interfaces and/or wireline interfaces that are configured to communicate with other network computing devices, including but not limited to, for example, other healthcare data processing system components (e.g., collector appliance 104, collector 106, recommendation engine 110, and system database 108 of healthcare data processing system 102 in FIG. 1), third party databases (e.g., NPID 126 in FIG. 1), other computing systems (e.g., the computing systems of providers 114-118 and the computing systems of insurer 120 in FIG. 1), and client devices (e.g., client device 128 in FIG. 1). In operation, the one or more communication interfaces 234 may include one or more wireline transceivers, such as Ethernet transceiver(s), Universal Serial Bus (USB) transceiver(s), or similar transceiver(s) configurable to communicate via a twisted pair wire, a coaxial cable, a fiber-optic link or a other type of physical connection to a wireline network. The one or more communication interfaces 234 may additionally or alternatively include one or more wireless transceivers, such as Bluetooth transceiver(s), Wi-Fi transceiver(s), WiMAX transceiver(s), and/or other types of wireless transceivers configurable to communicate via a wireless network.

In some embodiments, the communication interfaces 234 may be configured to provide reliable, secured, and/or authenticated communications. For each communication originating, terminating, or transiting the scheduling engine 220 described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms may be used as well or in addition to those listed herein to secure (and then decrypt/decode) provider-insurer messaging.

The data storage 238 includes one or more computer-readable storage media that can be read and/or written to by at least one of the processors 232. The one or more computer-readable storage media may include volatile and/or non-volatile storage components, such as optical, magnetic, organic or other memory or disc storage, which can be integrated in whole or in part with at least one of the processors 232. In some embodiments, the data storage 238 may be implemented using a single physical device (e.g., one optical, magnetic, organic or other memory or disc storage unit), while in other embodiments, the data storage 238 may be implemented using two or more physical devices.

The data storage 238 includes computer-readable program instructions 240 and perhaps additional data. In some embodiments, the data storage 238 may additionally include storage required to perform at least part of the herein-described techniques and/or at least part of the functionality of the herein-described systems and methods, including but not limited to the features and functions performed by a scheduling engine as disclosed and described herein.

The optional user interfaces 236 are operable to send data to and/or receive data from external user input/output devices. For example, the user interfaces 236 may be configured to send/receive data to/from user input devices such as a keyboard, a keypad, a touch screen, a computer mouse, a track ball, a joystick, and/or other similar devices, now known or later developed. The user interfaces 236 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interfaces 236 may also be configured to generate audible output(s), such as a speaker, speaker jack, audio output port, audio output device, earphones, and/or other similar devices, now known or later developed.

Example Collector Appliance Architecture

Figure 2C:
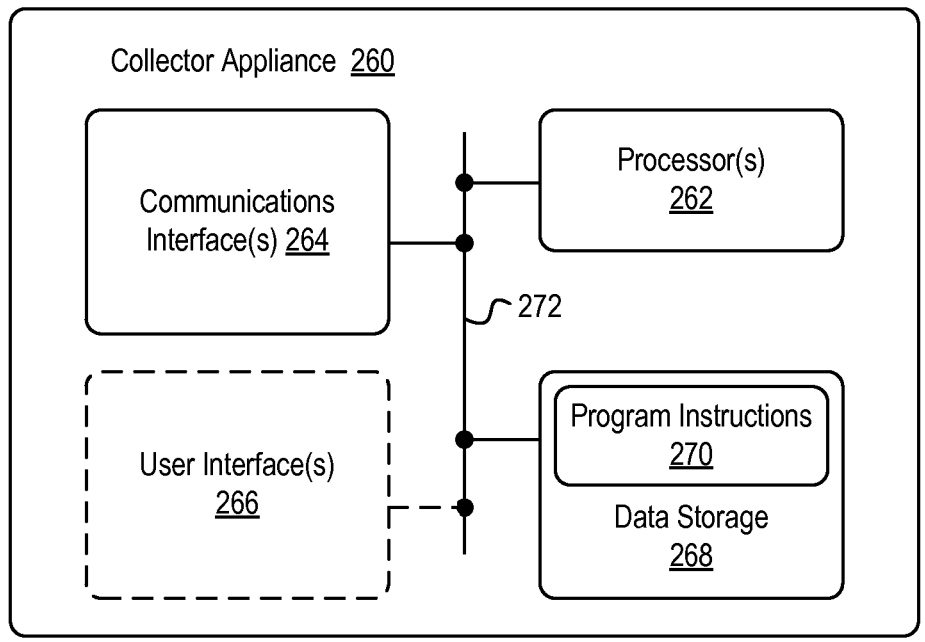
FIG. 2C shows a block diagram of an example collector appliance according to some embodiments of the disclosed systems and methods.

FIG. 2C shows a block diagram of an example collector appliance 260 according to some embodiments of the disclosed systems and methods. The example collector appliance 260 may be similar to or the same as the collector appliance 104 shown and described with reference to FIG. 1. In operation, the collector appliance 260 is specifically configured to interface with one or more of (i) at least one insurer computing system (e.g., insurer 120 in FIG. 1) and/or gateway (e.g., gateway 122 in FIG. 1), (ii) a collector (e.g., collector 106 in FIG. 1). The collector appliance 260 is specifically configured to perform the collector appliance functions disclosed and described herein.

The collector appliance 260 includes one or more processors 262, one or more communication interfaces 264, and data storage 268 configured to store computer readable instructions 240 for execution by the one or more processors 232, all of which are communicatively coupled to each other via a system bus, network, or other connection mechanism 272. In some embodiments, the collector appliance 260 may also include one or more user interfaces 266.

The one or more processors 262 may include one or more general purpose processors (e.g., microprocessors manufactured by Intel or Advanced Micro Devices) and/or one or more special purpose processors (e.g., digital signal processors, application specific integrated circuits, etc.). In operation, the one or more processors 262 are configured to execute the computer-readable program instructions 270 that are contained in the data storage 268 and/or other instructions as described herein. In some embodiments, the collector appliance 260 may comprise a field programmable gate array (FPGA) with a matrix of configurable logic blocks connected via programmable interconnects and programmed to perform the functions of the collector appliance described herein.

The one or more communications interfaces 264 may include one or more wireless interfaces and/or wireline interfaces that are configured to communicate with other network computing devices, including but not limited to, for example, other healthcare data processing system components (e.g., collector 106 in FIG. 1) and other computing systems (e.g., gateway 122 and the computing systems of insurer 120 in FIG. 1). In operation, the one or more communication interfaces 236 may include one or more wireline transceivers, such as Ethernet transceiver(s), Universal Serial Bus (USB) transceiver(s), or similar transceiver(s) configurable to communicate via a twisted pair wire, a coaxial cable, a fiber-optic link or a other type of physical connection to a wireline network. The one or more communication interfaces 264 may additionally or alternatively include one or more wireless transceivers, such as Bluetooth transceiver(s), Wi-Fi transceiver(s), WiMAX transceiver(s), and/or other types of wireless transceivers configurable to communicate via a wireless network.

In some embodiments, the communication interfaces 264 may be configured to provide reliable, secured, and/or authenticated communications between (i) the collector appliance and a collector, (ii) the collector appliance and a gateway, and (iii) the collector appliance and an insurer. For each communication originating, terminating, or transiting the collector appliance 260 described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms may be used as well or in addition to those listed herein to secure (and then decrypt/decode) provider-insurer messaging or copies thereof.

The data storage 268 includes one or more computer-readable storage media that can be read and/or written to by at least one of the processors 262. The one or more computer-readable storage media may include volatile and/or non-volatile storage components, such as optical, magnetic, organic or other memory or disc storage, which can be integrated in whole or in part with at least one of the processors 262. In some embodiments, the data storage 238 may be implemented using a single physical device (e.g., one optical, magnetic, organic or other memory or disc storage unit), while in other embodiments, the data storage 268 may be implemented using two or more physical devices.

The data storage 268 includes computer-readable program instructions 270 and perhaps additional data. In some embodiments, the data storage 268 may additionally include storage required to perform at least part of the herein-described techniques and/or at least part of the functionality of the herein-described systems and methods, including but not limited to the features and functions performed by a collector appliance as disclosed and described herein.

The optional user interfaces 266 are operable to send data to and/or receive data from external user input/output devices. For example, the user interfaces 266 may be configured to send/receive data to/from user input devices such as a keyboard, a keypad, a touch screen, a computer mouse, a track ball, a joystick, and/or other similar devices, now known or later developed. The user interfaces 266 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interfaces 266 may also be configured to generate audible output(s), such as a speaker, speaker jack, audio output port, audio output device, earphones, and/or other similar devices, now known or later developed.

Example Collector Architecture

Figure 2D:
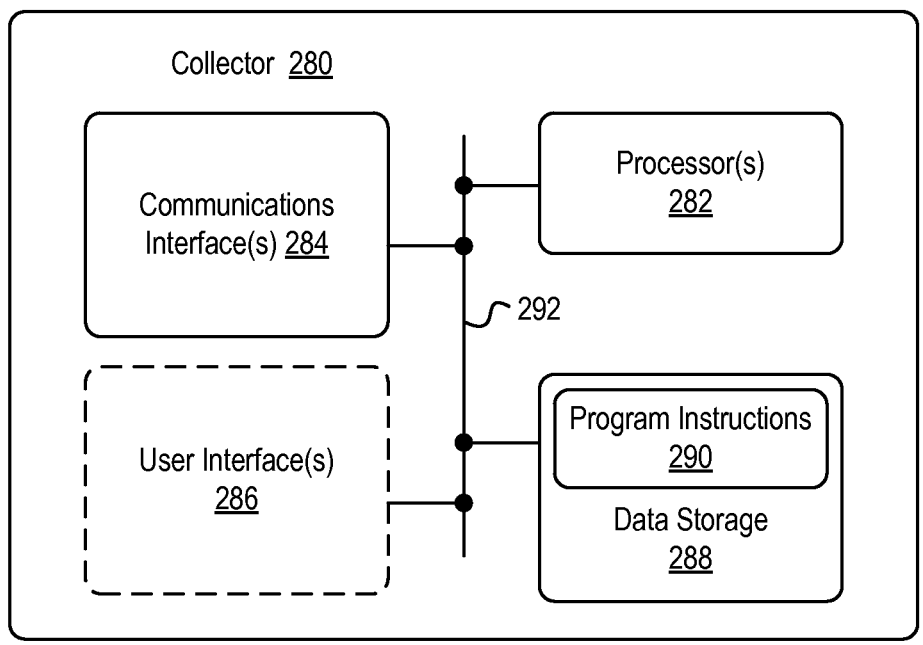
FIG. 2D shows a block diagram of an example collector according to some embodiments of the disclosed systems and methods.

FIG. 2D shows a block diagram of an example collector 280 according to some embodiments of the disclosed systems and methods. The example collector 280 may be similar to or the same as the collector 106 shown and described with reference to FIG. 1. In operation, the collector 280 is specifically configured to interface with one or more of (i) an insurer computing system (e.g., insurer 120 in FIG. 1), (ii) a gateway (e.g., gateway 122 in FIG. 1), (iii) a collector (e.g., collector 106 in FIG. 1), (iv) a recommendation engine (e.g., recommendation engine 110 in FIG. 1), (v) a system database (e.g., system database 108 in FIG. 1), and/or (vi) an NPID registry (e.g., NPID 126 in FIG. 1). The collector 280 is specifically configured to perform the collector appliance functions disclosed and described herein.

The collector 280 includes one or more processors 282, one or more communication interfaces 284, and data storage 288 configured to store computer readable instructions 290 for execution by the one or more processors 282, all of which are communicatively coupled to each other via a system bus, network, or other connection mechanism 292. In some embodiments, the collector 280 may also include one or more user interfaces 286.

The one or more processors 282 may include one or more general purpose processors (e.g., microprocessors manufactured by Intel or Advanced Micro Devices) and/or one or more special purpose processors (e.g., digital signal processors, application specific integrated circuits, etc.). In operation, the one or more processors 282 are configured to execute the computer-readable program instructions 290 that are contained in the data storage 288 and/or other instructions as described herein.

The one or more communications interfaces 284 may include one or more wireless interfaces and/or wireline interfaces that are configured to communicate with other network computing devices, including but not limited to, for example, other healthcare data processing system components (e.g., collector appliance 104 and recommendation engine 110 in FIG. 1) and other computing systems (e.g., gateway 122 and the computing systems of insurer 120 in FIG. 1). In operation, the one or more communication interfaces 284 may include one or more wireline transceivers, such as Ethernet transceiver(s), Universal Serial Bus (USB) transceiver(s), or similar transceiver(s) configurable to communicate via a twisted pair wire, a coaxial cable, a fiber-optic link or a other type of physical connection to a wireline network. The one or more communication interfaces 284 may additionally or alternatively include one or more wireless transceivers, such as Bluetooth transceiver(s), Wi-Fi transceiver(s), WiMAX transceiver(s), and/or other types of wireless transceivers configurable to communicate via a wireless network.

In some embodiments, the communication interfaces 284 may be configured to provide reliable, secured, and/or authenticated communications between (i) the collector and a collector appliance, (ii) the collector and a gateway, (iii) the collector and an insurer, and (iv) between the collector and other system components. For each communication originating, terminating, or transiting the collector 280 described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms may be used as well or in addition to those listed herein to secure (and then decrypt/decode) provider-insurer messaging or copies thereof.

The data storage 288 includes one or more computer-readable storage media that can be read and/or written to by at least one of the processors 282. The one or more computer-readable storage media may include volatile and/or non-volatile storage components, such as optical, magnetic, organic or other memory or disc storage, which can be integrated in whole or in part with at least one of the processors 282. In some embodiments, the data storage 288 may be implemented using a single physical device (e.g., one optical, magnetic, organic or other memory or disc storage unit), while in other embodiments, the data storage 288 may be implemented using two or more physical devices.

The data storage 288 includes computer-readable program instructions 290 and perhaps additional data. In some embodiments, the data storage 288 may additionally include storage required to perform at least part of the herein-described techniques and/or at least part of the functionality of the herein-described systems and methods, including but not limited to the features and functions performed by a collector as disclosed and described herein.

The optional user interfaces 286 are operable to send data to and/or receive data from external user input/output devices. For example, the user interfaces 286 may be configured to send/receive data to/from user input devices such as a keyboard, a keypad, a touch screen, a computer mouse, a track ball, a joystick, and/or other similar devices, now known or later developed. The user interfaces 286 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interfaces 266 may also be configured to generate audible output(s), such as a speaker, speaker jack, audio output port, audio output device, earphones, and/or other similar devices, now known or later developed.

Example Client Computing Device Architecture

Figure 3:
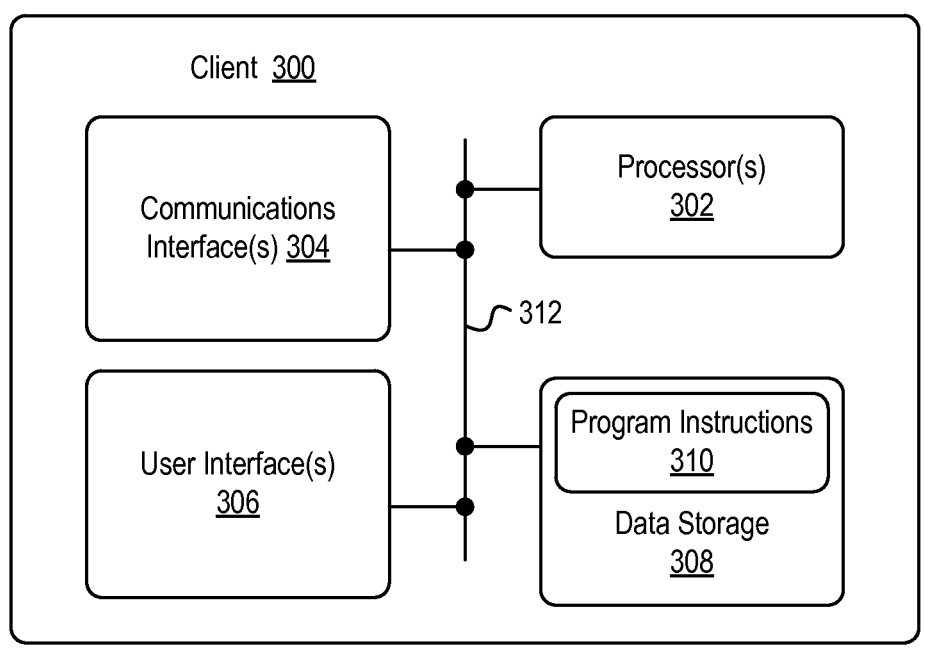
FIG. 3 shows a block diagram of an example client computing device according to some embodiments of the disclosed systems and methods.

FIG. 3 shows a block diagram of an example client computing device 300 according to some embodiments of the disclosed systems and methods. The example client computing device 300 (or simply client device) may be similar to or the same as (and may perform the same or similar functions as) any of the client devices described herein, including but not limited to the client device 170 shown and described with reference to FIG. 1. In some embodiments, the client device may be a laptop computer, desktop computer, tablet computer, smart phone, or other computing device.

The client device 300 includes one or more processors 302, one or more communication interfaces 304, data storage 308 configured to store computer readable instructions 310 for execution by the one or more processors 202, and one or more user interface 306, all of which are communicatively coupled to each other via a system bus, network, or other connection mechanism 312.

The one or more processors 302 may include one or more general purpose processors (e.g., microprocessors manufactured by Intel or Advanced Micro Devices) and/or one or more special purpose processors (e.g., digital signal processors, application specific integrated circuits, etc.). In operation, the one or more processors 302 are configured to execute the computer-readable program instructions 310 that are contained in the data storage 308 and/or other instructions as described herein.

The one or more communications interfaces 304 may include one or more wireless interfaces and/or wireline interfaces that are configured to communicate with other network computing devices, including but not limited to, for example, components of the healthcare data processing system (e.g., recommendation engine 110 and/or the scheduling engine 112 shown and described with reference to FIGS. 1, 2A, and 2B) and other computing systems (e.g., the computing systems of providers 118-122 and the computing systems of insurers 124-128 shown and described with reference to FIG. 1). In operation, the one or more communication interfaces 304 may include one or more wireline transceivers, such as Ethernet transceiver(s), Universal Serial Bus (USB) transceiver(s), or similar transceiver(s) configurable to communicate via a twisted pair wire, a coaxial cable, a fiber-optic link or a other type of physical connection to a wireline network. The one or more communication interfaces 304 may additionally or alternatively include one or more wireless transceivers, such as Bluetooth transceiver(s), Wi-Fi transceiver(s), WiMAX transceiver(s), 3G transceiver(s), 4G transceiver(s), LTE transceiver(s), and/or other types of wireless transceivers configurable to communicate via a wireless network.

In some embodiments, the communication interfaces 304 may be configured to provide reliable, secured, and/or authenticated communications. For each communication originating or terminating at the client device 300 described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms may be used as well or in addition to those listed herein to secure (and then decrypt/decode) provider-insurer messaging.

The data storage 308 includes one or more computer-readable storage media that can be read and/or written to by at least one of the processors 302. The one or more computer-readable storage media may include volatile and/or non-volatile storage components, such as optical, magnetic, organic or other memory or disc storage, which can be integrated in whole or in part with at least one of the processors 302. In some embodiments, the data storage 308 may be implemented using a single physical device (e.g., one optical, magnetic, organic or other memory or disc storage unit), while in other embodiments, the data storage 308 may be implemented using two or more physical devices.

The data storage 308 includes computer-readable program instructions 310 and perhaps additional data. In some embodiments, the data storage 308 may additionally include storage required to perform at least part of the herein-described techniques and/or at least part of the functionality of the herein-described systems and methods, including but not limited to the features and functions performed by a client device as disclosed and described herein.

The user interfaces 306 are operable to send data to and/or receive data from external user input/output devices. For example, the user interfaces 306 may be configured to send/receive data to/from user input devices such as a keyboard, a keypad, a touch screen, a computer mouse, a track ball, a joystick, and/or other similar devices, now known or later developed. The user interfaces 306 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interfaces 306 may also be configured to generate audible output(s), such as a speaker, speaker jack, audio output port, audio output device, earphones, and/or other similar devices, now known or later developed.

Example Recommendations and Predictions Displayed by Client Devices

FIGS. 4A-4C show example recommendations and predictions that a patient's smartphone or tablet displays in response to receiving one or more messages from a scheduling engine, such as scheduling engine 112 (FIG. 1), where the one or more messages comprise one or more of the first provider, the expected patient cost for the first provider to perform the medical procedure, a patient rating for the first provider, the second provider, the expected patient cost for the second provider to perform the medical procedure, a patient rating for the second provider, a follow-up provider. Although the examples shown in FIGS. 4A-C show recommendations displayed on a smartphone or tablet, in other embodiments, similar displays can be shown within a graphical user interface of a patient's desktop or laptop computer as well.

FIG. 4A shows components of an example recommendation 402 displayed within a graphical user interface 414 of a client device 400 according to some embodiments of the disclosed systems and methods. Example recommendation 402 is useful when a patient has scheduled an appointment to have a medical provider perform a medical procedure some time in the future, and there are other medical providers in the general area that could perform the same medical procedure for the patient for a lower out-of-pocket cost for the patient.

The example recommendation 402 includes a first field 404 that shows the expected out-of-pocket cost for a first provider to perform a medical procedure. In this example, the first provider is a provider that the patient has made an appointment with to perform the medical procedure. As described herein, a recommendation engine (e.g., recommendation engine 110 in FIG. 1) determines the expected out-of-pocket costs for the patient to have the first provider perform the medical procedure, and a scheduling engine (e.g., scheduling engine 112 in FIG. 1) sends the expected out-of-pocket cost to the patient's client device.

The example recommendation 402 also includes a second field 406 that shows the expected out-of-pocket cost for a second provider (an alternative provider) to perform the medical procedure. In this example, the second provider is an alternative provider that the recommendation engine (e.g., recommendation engine 110 in FIG. 1) has selected from a set of one or more alternative providers that are located within a threshold geographic distance (e.g., within about 10 miles or perhaps more) from the first provider. As described in more detail with respect to FIG. 5, the set of one or more alternative providers may also be limited to only alternative providers that have a patient rating above a threshold and/or who are available to perform the medical procedure with some threshold number of days from the patient's appointment with the first provider. In operation, the expected patient out-of-pocket costs for the second provider (the one selected by the recommendation engine) to perform the medical procedure for the patient are less than the expected out-of-pocket costs for the first provider (the originally-scheduled provider) to perform the medical procedure for the patient.

The example recommendation 402 also includes a third field 408 that asks if the patient would like to reschedule the medical procedure to be performed by the second provider rather than the first provider. The recommendation 402 also includes a "Yes" icon 410 and a "No" icon 412 via which the patient can respond to the prompt in the third field 408.

In response to the patient selecting the "Yes" icon 410, the client device 400 may inform the scheduling engine 112 (FIG. 1) of the patient's selection, and in response, receive data from the scheduling engine for scheduling an appointment for the second provider to perform the medical procedure. The data for scheduling the appointment with the second provider may include, for example, the address, phone number, website, link to the second provider's online scheduling application (if applicable), and/or other information for scheduling the appointment. After receiving scheduling data from the scheduling engine, the patient's client device displays, within the GUI, some or all of the scheduling data to the patient. For example, the patient's client device may display the second provider's street address, the second provider's phone number, a link to call the second provider, and/or a link that opens a scheduling application that enables the patient to schedule the medical procedure at the second provider.

Similarly, in response to the patient selecting the "No" icon 412, the client device 400 may simply close the recommendation 402. However, in some embodiments, the client device 400 may present one or more additional recommendations for one or more subsequent providers with expected patient out-of-pocket costs for each subsequent provider. The additional recommendation(s) may look substantially the same as recommendation 402 except that second field 406 displays the name of and expected patient out-of-pocket cost for a subsequent provider (rather than the second provider), and the third field 408 asks if the patient would like to reschedule the medical procedure to be performed by the subsequent provider (rather than the second provider).

FIG. 4B shows components of another example recommendation 430 displayed within a graphical user interface 414 of a client device 400 according to some embodiments of the disclosed systems and methods. Example recommendation 430 is useful in situations where the first provider has the lowest expected out-of-pocket cost for the patient within the threshold geographic range but one or more alternative providers within the threshold geographic distance of the first provider has a patient rating that is higher than the patient rating of the first provider.

The example recommendation 430 includes a first field 432 that shows a patient rating for the first provider. In this example, the first provider is a provider that the patient has made an appointment with to perform the medical procedure.

The example recommendation 430 also includes a second field 434 that shows a patient rating for the second provider. In this example, the second provider is an alternative provider that the recommendation engine (e.g., recommendation engine 110 in FIG. 1) has selected from a set of one or more alternative providers that are located within a threshold geographic distance (e.g., within about 10 miles or perhaps more) from the first provider. In operation, the patient rating for the second provider (the one selected by the recommendation engine) is higher than the patient rating for the first provider (the originally-scheduled provider)

In operation, the recommendation engine (e.g., recommendation engine 110 in FIG. 1) can obtain a patient rating for the first provider and the second provider from a system database (e.g., system database 108 in FIG. 1), where the system database stores a history of ratings that patients have given providers after having a procedure performed by the provider. In some embodiments, the patient rating may be a patient rating for the procedure performed by the provider rather than just an overall patient rating for the provider.

Recommendation 430 also includes a third field 436 that asks if the patient would like to reschedule the medical procedure to be performed by the second provider rather than the first provider. The recommendation 430 also includes a "Yes" icon 410 and a "No" icon 412 via which the patient can respond to the prompt in the third field 436.

In response to the patient selecting the "Yes" icon 410, the client device 400 may inform the scheduling engine 112 (FIG. 1) of the patient's selection, and in response, the client device receives data from the scheduling engine for scheduling an appointment for the second provider to perform the medical procedure. The data for scheduling the appointment with the second provider may include, for example, the address, phone number, website, link to the second provider's online scheduling application (if applicable), and/or other information for scheduling the appointment. After receiving scheduling data from the scheduling engine, the patient's client device displays, within the GUI, some or all of the scheduling data to the patient. For example, the patient's client device may display the second provider's street address, the second provider's phone number, a link to call the second provider, and/or a link that opens a scheduling application that enables the patient to schedule the medical procedure at the second provider.

Similarly, in response to the patient selecting the "No" icon 412, the client device 400 may simply close the recommendation 430. However, in some embodiments, the client device 400 may present one or more additional recommendations for one or more subsequent providers with patient ratings for each subsequent provider. The additional recommendation(s) may look substantially the same as recommendation 430 except that second field 434 displays the name of and patient rating for a subsequent provider (rather than the second provider), and the third field 436 asks if the patient would like to reschedule the medical procedure to be performed by the subsequent provider (rather than the second provider).

FIG. 4C shows components of another example recommendation 460 displayed within a graphical user interface 414 of a client device 400 according to some embodiments of the disclosed systems and methods. Recommendation 460 is useful in situations where the patient is at the point of service (e.g., at a doctor's office or clinic), or perhaps will be at the point of service within the near future, where a medical professional will be recommending that the patient obtain some follow-up treatment or procedure. For example, a doctor at a doctor's office or clinic may recommend that the patient obtain an MRI/CT scan and may also tell the patient where to obtain the MRI/CT scan. Some patients may be wary of going somewhere other than where their doctor has recommended, so recommendation 460 enables patients to ask their doctor about alternative providers during their appointment.

The example recommendation 460 includes a first field 462 that shows (i) a prediction of a particular follow-up procedure that the patient's doctor is likely to recommend and (ii) a proposed follow-up provider to perform the follow-up procedure for the patient. As described in more detail with reference to FIG. 5, the recommendation engine (e.g., recommendation engine 110 in FIG. 1) is configured to predict the follow-up procedure based at least in part on the on the doctor's specialty (typically obtained from the NPI Registry 162 in FIG. 1), the patient's health records (typically obtained from the patient's insurer), a history of follow-on procedures that that doctor tends to recommend (typically obtained from the insurer), and perhaps other factors.

Additionally, as described in more detail with reference to FIG. 5, the recommendation engine is also configured to select a proposed follow-up provider to perform the predicted follow-up procedure from a set of potential follow-up providers that are in the same general geographic area as the first provider (e.g., the doctor's office where the physician is likely to recommend the predicted follow-up procedure). In this example, the follow-up provider displayed in the recommendation 460 is a follow-up provider in the same general geographic area as the patient's doctor that has the lowest expected out-of-pocket cost for the patient. In some embodiments, the recommendation engine may additionally consider patient ratings when recommending a proposed follow-up provider for the predicted follow-up procedure. Rather than selecting the proposed follow-up provider just based on cost, the recommendation engine can select the follow-up provider that has the lowest cost from a subset of potential follow-up providers that all have at least a minimum patient rating. For example, if the minimum patient rating is 3 out of 5 stars, then as between a first potential follow-up provider with an expected out-of-pocket cost of $50 and a patient rating of 2, a second potential follow-up provider with an expected out-of-pocket cost of $75 and a patient rating of 4, and a third potential follow-up provider with an expected out-of-pocket cost of $100 and a patient rating of 4, the recommendation engine would select the second potential follow-up provider as the proposed follow-up provider because the second provider has the lowest expected out-of-pocket cost among the potential follow-up providers having a patient rating of 3 or higher.

The example recommendation 460 also includes a second field 464 that shows the expected out-of-pocket cost for the proposed follow-up provider to perform the predicted follow-up procedure. As described herein, a recommendation engine (e.g., recommendation engine 110 in FIG. 1) determines the expected out-of-pocket costs for the patient to have the proposed follow-up provider perform the predicted follow-up procedure, and a scheduling engine (e.g., scheduling engine 112 in FIG. 1) sends the expected out-of-pocket cost to the patient's client device.

The example recommendation 460 also includes a third field 466 that shows a patient rating for the proposed follow-up provider. In operation, the recommendation engine can obtain a patient rating for the proposed provider from the system database, where the system database stores a history of ratings that patients have given providers after having a procedure performed by the provider.

The example recommendation 460 also includes a fourth field 468 that asks if the patient would like to schedule the predicted follow-up procedure to be performed by the proposed follow-up provider. The recommendation 460 also includes a "Yes" icon 410 and a "No" icon 412 via which the patient can respond to the prompt in the fourth field 468.

In response to the patient selecting the "Yes" icon 410, the client device 400 may inform the scheduling engine 112 (FIG. 1) of the patient's selection, and in response, the client device receives data from the scheduling engine for scheduling an appointment for the proposed follow-up provider to perform the predicted follow-up procedure. The data for scheduling the appointment with the proposed follow-up provider may include, for example, the address, phone number, website, link to the proposed follow-up provider's online scheduling application (if applicable), and/or other information for scheduling the appointment. After receiving scheduling data from the scheduling engine, the patient's client device displays, within the GUI, some or all of the scheduling data to the patient. For example, the patient's client device may display the follow-up provider's street address, the follow-up provider's phone number, a link to call the follow-up provider, and/or a link that opens a scheduling application that enables the patient to schedule the follow-up procedure at the follow-up provider.

Similarly, in response to the patient selecting the "No" icon 412, the client device 400 may simply close the recommendation 460. However, in some embodiments, the client device 400 may present one or more additional recommendations for one or more subsequent proposed follow-up providers with patient ratings for each subsequent proposed follow-up provider. The additional recommendation(s) may look substantially the same as recommendation 460 except that second field 434 displays the name of and patient rating for a subsequent proposed follow-up provider (rather than the previously proposed follow-up provider), and the third field 436 asks if the patient would like to reschedule the follow-up procedure to be performed by the subsequent proposed follow-up provider (rather than the previously-proposed follow-up provider).

Example Methods

Figure 5:
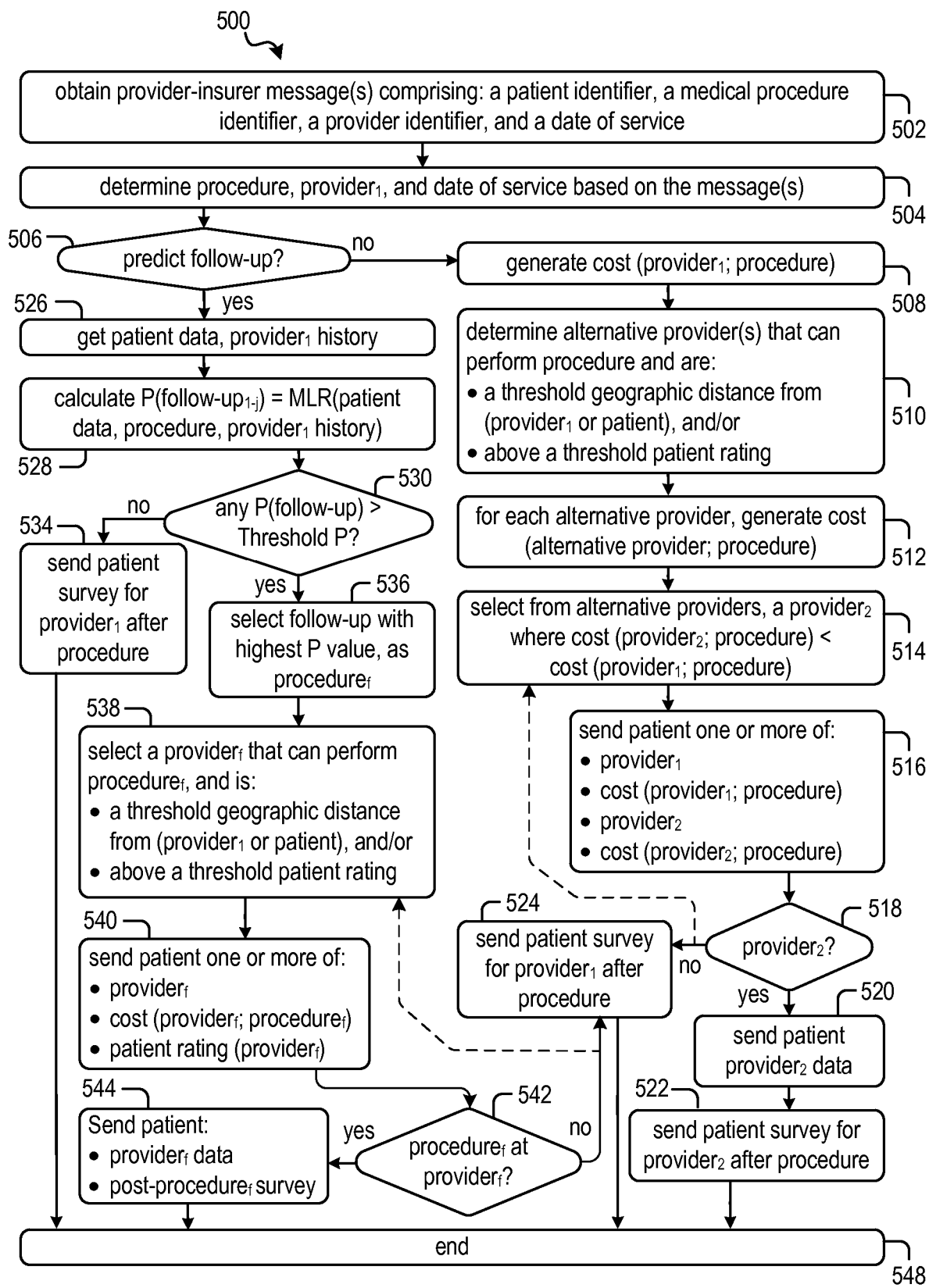
FIG. 5 shows an example flow chart according to some embodiments of the disclosed systems and methods.

FIG. 5 shows an example method 500 according to some embodiments. In operation, method 500 is implemented by a healthcare recommendation and prediction system, such as system 102 described herein with reference to FIG. 1.

Method 500 begins at method block 502, where the system obtains (e.g., receiving, copying, or receiving a copy of) one or more provider-insurer messages. The one or more provider-insurer messages include either or both of (i) request message(s) sent from a provider to an insurer and/or (ii) response message(s) sent from an insurer to a provider. In operation, the one or more provider-insurer messages comprise (individually or in combination) at least (i) a patient identifier, (ii) a medical procedure identifier, (iii) a provider identifier, and (iv) a date of service. In some embodiments, the one or more provider-insurer messages include one or more of a HIPAA HETS 270 Request, 271 Response, 278 Request, and/or 278 Response. However, the provider-insurer messages may include other types of provider requests and insurer responses that include information about a patient, a prospective medical procedure, a healthcare provider, and a date of service on which the healthcare provider will provide the prospective procedure.

In some embodiments, method block 502 may include a collector appliance (FIG. 1) obtaining a provider-to-insurer message (e.g., a 270 Request or a 278 Request), and sending a copy of the provider-to-insurer message to a recommendation engine (FIG. 1) either directly or via a collector (FIG. 1). Method block 502 may additionally or alternatively include the collector appliance obtaining an insurer-to-provider message (e.g., a 271 Response or a 278 Response), and sending a copy of the insurer-to-provider message to the recommendation engine directly or via a collector. In some embodiments, method block 502 may additionally or alternatively include the collector appliance obtaining a provider-to-insurer message (e.g., a 270 Request or a 278 Request), sending a "dummy" provider-to-insurer message (e.g., a dummy 270 Request or 278 Request) to an insurer, receiving a "dummy" insurer-to-provider message (e.g., a dummy 271 Response or 278 Response) in response, and then sending the "dummy" insurer-to-provider message to the recommendation engine directly or via a collector.

After obtaining the one or more provider-insurer messages at block 502, method 500 advances to block 504, where the system determines a medical procedure (generally referred to herein as a procedure), a first provider (provider$_1$ in FIG. 5), and a date of service based on the procedure identifier, provider identifier, and data of service in the one or more provider-insurer messages. Block 502 may also include determining the patient based on the patient identifier in the one or more provider-insurer messages.

In some embodiments, determining the procedure includes looking up the procedure identifier from the obtained message in a table of procedure identifiers. In some embodiments, the procedure identifier may include multiple components. For example, the procedure identifier may include one or more of (i) a medical service type or category of service (e.g., medical imaging) and (ii) a current procedure type (e.g., MRI/CT Scan, bone scan). Because different insurers may use different procedure identifiers, some embodiments may include looking up the procedure identifier from the obtained message in an insurer-specific table of procedure identifiers stored in a system database (FIG. 1) or other data storage system. In some embodiments, the collector accesses the table of procedure identifiers in the system database to determine the procedure based on the procedure identifier. In other embodiments, the collector appliance or the recommendation engine may instead access the table of procedure identifiers to determine the procedure based on the procedure identifier.

In some embodiments, determining the first provider includes looking up the provider identifier from the obtained message in a table of provider identifiers. In some embodiments, the table of provider identifiers is stored in the National Provider Identifier (NPID) Registry (FIG. 1). In some embodiments, the provider identifier includes the provider's name (e.g., Bone and Joint Associates) and the provider's specialty (e.g., orthopedics). Some embodiments may additionally include cross-referencing the provider identifier with a table of provider specialties stored in the system database (FIG. 1) or other data storage system to determine both the identity of the provider and the provider's specialty. In some embodiments, the collector determines the first provider (and also perhaps the first provider's specialty) based on the provider identifier. In other embodiments, the collector appliance or the recommendation engine may instead access the table of provider identifiers to determine the first provider (and also perhaps the first provider's specialty) based on the procedure identifier from the obtained one or more provider-insurer messages.

Next, method 500 advances to method block 506, where the system determines whether to predict a follow-up procedure. To determine whether to predict a follow-up procedure, the system considers at least the procedure and the first provider, but the system may consider other factors too when determining whether to predict a follow-up procedure. In operation, determining whether to predict a follow-up may include determining that a follow-up prediction is required when the procedure and first provider match certain preconfigured rules. For example, if the procedure is "office visit" and the first provider's specialty is "general physician," then it is likely that the patient may be instructed to obtain one or more follow-up procedures, e.g., imaging, lab work, a specialist's assessment, etc. Other combinations of procedure and first provider (alone or in combination with perhaps other factors) may cause the system to predict a follow-up procedure.

If the system determines that it should predict a follow-up procedure, then method 500 advances to block 526, but if the system determines that a follow-up procedure prediction is not warranted, then method 500 advances to block 508. The case where prediction of a follow-up procedure is not required is described first, and then the case where prediction of a follow-up procedure is required (or at least desired) is described afterwards.

At method block 508, the system generates an expected patient cost for the first provider to perform the medical procedure for the patient. In operation, the system generates the expected out-of-pocket cost for the patient to have the first provider perform the procedure based on one or more of (i) whether the insurer covers the medical procedure, (ii) billing and/or payment history between the first provider and the insurer for the medical procedure, (iii) whether the first provider and the insurer have an agreed-upon price to perform the medical procedure, (iv) whether the first provider participates in an insurance plan that the patient has purchased from the insurer, and/or (v) the patient's copay and deductible status. In some embodiments, the generating the expected out-of-pocket cost for the first provider to perform the procedure includes accessing a database of procedure pricing based on historical billing and pricing information. In operation, the system database (FIG. 1) may contain procedure pricing based on the historical billing and pricing information between the insurer and the provider. Additionally or alternatively, the system may access the National Consumer Cost Tool (NCCT) from the Blue Cross and Blue Shield Association (BSBCA) or another commercially available database to obtain procedure pricing information. Additionally or alternatively, the system may create and send a "dummy claim" (e.g., an 837 Professional Health Care Claim message or similar) to the insurer that specifies the patient, the procedure, and the first provider. In response to receiving the "dummy claim" (e.g., the 837 Claim or similar), the insurer generates and sends the system a response with the "dummy claim" payment information (e.g., an 835 Health Care Claim Payment/Advice message or similar) that includes the charges for the procedure, whether there is a deductible, co-insurance and/or copay for the patient and other payment information. The system then uses the information in the response (e.g., the 835 message or similar) from the insurer to generate the expected out-of-pocket cost for the first provider to perform the procedure.

Next, method 500 advances to method block 510, where the system determines a set of one or more alternative providers that can perform the procedure, where the set of one or more alternative providers is limited to only alternative providers that are located within a threshold geographic distance of the first provider (or perhaps within a threshold geographic distance of the patient). In some embodiments, the system determines whether a particular alternative provider is available to perform the medical procedure identified in the provider-insurer messaging by accessing a database comprising correlations between providers and the medical procedures that each provider performs. In operation, correlations between a provider and the medical procedures that the provider performs may be stored in the system database (FIG. 1) and updated periodically by information obtained from the provider or an insurer.

In some embodiments, the system identifies alternative providers within a threshold geographic distance (e.g., within 5 miles, within 10 miles, etc.) of the first provider (or perhaps the patient) by reference to a geographic information system (GIS) database comprising a list of providers and each provider's geographic location (e.g., street address). In some embodiments, the GIS database may be a component of the system database (FIG. 1).

In some embodiments, the set of one or more alternative providers may be further limited to only alternative providers that are (i) above a threshold patient rating and/or (ii) available to perform the medical procedure within a threshold timeframe of the date of service identified in the obtained provider-insurer messaging.

In embodiments where the system uses a threshold patient rating as a factor for selecting the set of one or more alternative providers, the system can access patient rating data that includes patient ratings of providers and/or patient ratings of procedures performed by providers. For example, one provider may have a generally high patient rating overall, but have low patient ratings for a certain procedure or procedures. Likewise, a provider may have a generally low patient rating overall, but have high patient ratings for a certain procedure or procedures. In operation, the system can use the patient ratings of providers, patient ratings of procedures performed by providers, or some combination of the two as a factor (or factors) to consider when limiting the set of alternative providers to only providers that are above a threshold patient rating. In operation, the system obtains patient ratings of provider and procedures performed by providers from patient feedback or perhaps from other sources. In some embodiments, patient ratings of provider and/or procedures are stored in the system database (FIG. 1) or another data storage system.

In embodiments where the system further limits the set of alternative providers to only alternative providers that are available to perform the medical procedure within a threshold timeframe (e.g., up to +/−10-14 days, depending on the difference between the current date and the date of service) from the date of service identified in the provider-insurer messaging, the system can access scheduling systems at individual alternative providers to determine which alternative providers have available appointments to perform the procedure within the threshold timeframe of the date of service. Alternatively, in some embodiments, the system can determine or at least infer whether a particular alternative provider likely has available appointments to perform the procedure based on an analysis of provider-insurer messages exchanged between insurers and the particular alternative provider that refer to the same procedure (i.e., include the same procedure identifier).

After determining the set of one or more alternative providers at method block 510, method 500 advances to method block 512, where the system determines, for each alternative provider in the set of one or more alternative providers from block 510, the patient's expected out-of-pocket cost to have the alternative provider perform the procedure. In operation, the system determines the expected out-of-pocket cost for each alternative provider perform the procedure in the same way that the system determines the expected out-of-pocket cost for the first provider to perform the procedure, as described with reference to method block 508.

Next, method 500 advances to method block 514 where the system selects a second provider from the set of one or more alternative providers, where the expected out-of-pocket patient cost for the second provider perform the procedure for the patient that is less than the expected out-of-pocket patient cost for the first provider to perform the procedure for the patient.

Some embodiments may additionally or alternatively use patient rating to select the second provider from the set of one or more alternative providers. For example, if two alternative providers have the same or substantially the same expected out-of-pocket cost for the patient, then the system may, in some embodiments, additionally consider patient rating, and select the alternative provider having the higher patient rating as the second provider.

After the system has selected the second provider at block 514, method 500 advances to method block 516, wherein the system generates and sends the patient (i.e., a client device associated with the patient) one or more messages, wherein the one or more messages (individually or in combination) comprise (i) the first provider, (ii) the patient's expected out-of-pocket cost for the first provider to perform the procedure, (iii) the second provider, and (iv) the patient's expected out-of-pocket cost for the second provider to perform the procedure. In some embodiments, the scheduling engine (FIG. 1) alone or in combination with the recommendation engine (FIG. 1) generates and sends the one or more messages to the patient's client device.

In response to receiving the one or more generated messages from the system, the patient's client device displays recommendations based on the one or more messages (or information contained in the messages) within a graphical user interface on the patient's client device (or perhaps associated with the patient's client device). In operation, the recommendations displayed by the patient's client device may be the same as or similar to the example recommendations shown and described with reference to FIGS. 4A and 4B.

After the system has generated and sent the one or more messages to the patient's client device in method block 516, method 500 advances to method block 518, where the system receives feedback from the patient's client device as to whether (i) the patient wishes to schedule an appointment with the second provider to perform the procedure or (ii) not schedule an appointment with the second provider to perform the procedure. In some embodiments, and as described in more detail with reference to the examples shown in FIGS. 4A and 4B, the patient's client device asks the patient whether he/she wishes to schedule the procedure with the second provider along with a Yes/No prompt. In such embodiments, the client device is configured to (i) inform the system (e.g., via a message or other signaling from the client device to the system) that the patient wishes to schedule the procedure with the second provider in response to receiving an input from the patient indicating that the patient wishes to schedule the procedure with the second provider (e.g., the Yes prompt) or (ii) inform the system (e.g., via a message or other signaling from the client device to the system) that the patient does not wish to schedule the procedure with the second provider in response to receiving an input from the patient indicating the patient does not wish to schedule the procedure with the second provider (e.g., the No prompt).

At method block 518, if the patient's client device informs the system that the patient wishes to schedule the procedure with the second provider, then method 500 advances to block 520, where the system sends the patient's client device information for scheduling the procedure with the second provider, e.g., the phone number (or a link to the phone number) of the second provider, a link to the second provider's web page, a link to the second provider's online scheduling application, and/or other information for the patient's client device to display to the patient for scheduling the procedure with the second provider. The system later determines whether the patient actually follows through with scheduling the procedure with the second provider based on the provider-insurer messaging between the second provider and the insurer when the patient schedules the procedure with second provider. And because the provider-insurer messaging includes a date of service, the system further knows the date when the second provider will perform the procedure for the patient.

After the date that the second provider has performed the procedure for the patient, then at method block 522, the system sends the patient's client device a patient survey to obtain patient rating information on the second provider and/or the procedure performed by the second provider. In some embodiments, block 522 may also include receiving and storing patient's completed survey (or at least the patient rating information contained therein) in the system database (FIG. 1) future reference. After block 522, method 500 ends at method block 548.

But if at method block 518, the patient's client device informs the system that the patient does not wish to schedule the procedure with the second provider (or if the system receives no further information from the patient's client device regarding the procedure), then method 500 advances to block 524 where, after the date that the first provider has performed the procedure, the system sends the patient's client device a patient survey to obtain patient rating information on the first provider and/or the procedure performed by the first provider. In some embodiments, block 524 may also include receiving and storing patient's completed survey (or at least the patient rating information contained therein) in the system database (FIG. 1) future reference. After block 524, method 500 ends at method block 548.

In some embodiments, if the patient's client device informs the system that the patient does not wish to schedule the procedure with the second provider, then method 500 returns to block 514, where the system selects another provider from the set of one or more alternative providers, sets the newly-selected provider as the "second provider", and then proceeds through method blocks 516-518 as described above with this newly-selected provider as the "second provider." In some embodiments, the system may cycle through steps 514-518 with multiple alternative providers from the set of one or more alternative providers determined at block 510.

Alternatively, in some embodiments, at method block 514, rather than selecting a single second provider from the set of one or more alternative providers, the system may instead select the top 2-5 alternative providers from the set of one or more alternative providers. In some embodiments, the system may select the top 2-5 alternative providers based on expected out-of-pocket cost for the patient, distance from the patient (or the first provider), and/or patient rating.

Then, at method block 516, the system alternatively generates and sends a message (e.g., an email or other type of message) with (i) a list of the top 2-5 alternative providers, (ii) the corresponding expected out-of-pocket cost for each of the top 2-5 alternative providers, and (iii) contact information (e.g., phone number, webpage, link to scheduling system (if applicable), or other contact information) for the patient to use in scheduling the procedure with the top 2-5 alternative providers. In some embodiments, the message may additionally include patient ratings for each of the top 2-5 alternative providers. In such embodiments, the system can later determine whether the patient scheduled an appointment to have one of the top 2-5 alternative perform the procedure, and after the date of the procedure, send a patient survey to the patient's client device, similar to method blocks 522 and 524.

Returning to method block 506 where the system determines whether to predict a follow-up procedure, if the system determines that prediction of a follow-up procedure is warranted, then method 500 advances to method block 526, where the system obtains patient data and first provider data. The patient data includes any of (i) patient demographic data (e.g., age, gender, ethnicity, national origin, occupation, education, income, address, family status, and/or other demographic data), and/or (ii) patient health data (e.g., known diseases, allergies, current medications, past medications, doctor visit history, family history of disease, prior injuries/treatments, and/or other health data). The first provider data includes the first provider's specialty, the follow-up procedures that the first provider has prescribed in the past, and/or other data about the first provider. In some embodiments, the patient data and provider are obtained from the insurer and stored in the system database (FIG. 1).

After obtaining the patient data and the first provider data at block 526, the method 500 advances to method block 528, where the system performs a Multinomial Logistic Regression analysis to predict a follow-up procedure, where (i) the predictor variables for the regression analysis include at least the procedure (determined at method block 504), the patient data (obtained at method block 526), and the first provider data (obtained at method block 526) and (ii) the response variables are all of the potential follow-up procedures in a set of potential follow-up procedures. In some embodiments, the set of potential follow-up procedures may include up to every procedure for which there is a procedure identifier. In other embodiments, the set of potential follow-up procedures may be limited to a predetermined set based on the procedure determined at method block 504. For example, if the procedure determined at method block 504 is "Office Visit—Orthopedic Specialist," the set of potential follow-up procedures might include follow-up procedures that are most-commonly associated with orthopedic office visits (e.g., bone scan, MRI, CT scan, X-ray, physical therapy) but exclude follow-up procedures that would not typically follow from an orthopedic office visit (e.g., electrocardiogram, cardiac stress testing, colonoscopy, mammogram).

The result of the Multinomial Logistic Regression analysis in method block 528 is a set of probabilities that includes, for each of the potential follow-up procedures in the set of potential follow-up procedures, a probability that the first provider will prescribe or recommend that follow-up procedure. In operation, the Multinomial Logistic Regression analysis may be any type of Multinomial Logistic Regression analysis such as a Classical Multinomial Logistic Regression analysis, a Naïve Bayes analysis, a Random Forests analysis, or other type of analysis that predicts probabilities for a plurality of possible discrete outcomes of a categorically distributed dependent variable based on a set of independent variables.

After calculating the probabilities for each potential follow-up procedure in the set of potential follow-up procedures at block 528, method 500 advances to method block 530, where the system determines whether any of the calculated probabilities for the potential follow-up procedures exceed a threshold probability. For example, if the threshold probability is 25%, then the system will determine whether any of the potential follow-up probabilities have a probability (as determined in method block 528) that is greater than 25% (or perhaps greater than or equal to 25%), i.e., whether there is at least a 25% chance that the first provider will prescribe the follow-up procedure based on the procedure, the patient data, and the first provider data (obtained in method block 526). Other threshold probabilities could be used as well.

If at method block 530, the system determines that there is no potential follow-up procedure in the set of potential follow-up procedures with a calculated probability that is greater than the threshold probability, then method 500 advances to method block 534, where, after the first provider has performed the procedure (i.e., after the date of service of the procedure as determined in method block 504), the system sends the patient's client device a patient survey to obtain patient rating information on the first provider and/or the procedure performed by the first provider. In some embodiments, block 534 may also include receiving and storing the patient's completed survey (or at least the patient rating information contained therein) in the system database (FIG. 1) future reference. After block 534, method 500 ends at method block 548.

But if at method block 530, the system determines that there is one or more potential follow-up procedures in the set of potential follow-up procedures with a calculated probability that is greater than the threshold probability, then method 500 advances to method block 536, where the system selects the follow-up procedure (procedure$_f$) from the set of potential follow-up procedures that has the highest probability.

After selecting the follow-up procedure (procedure$_f$) at method block 536, method 500 advances to method block 538, where the system determines a follow-up provider (provider$_f$) that can perform the follow-up procedure. In operation, the system determines and selects a follow-up provider in method block 538 in a manner similar that described with reference to method blocks 510-514.

In particular, method block 538 includes determining a set of one or more potential follow-up providers that can perform the follow-up procedure, where the set of one or more potential follow-up providers is limited to only potential follow-up providers that are located within a threshold geographic distance of the first provider (or perhaps within a threshold geographic distance of the patient). In some embodiments, the system determines whether a particular potential follow-up provider is available to perform the follow-up procedure selected in block 536 by accessing a database comprising correlations between the potential follow-up providers and the procedures that each potential follow-up provider performs. In operation, correlations between a provider and the procedures that the provider performs may be stored in the system database (FIG. 1) and updated periodically by information obtained from the provider or an insurer.

In some embodiments, the system identifies potential follow-up providers within a threshold geographic distance (e.g., within 5 miles, within 10 miles, etc.) of the first provider (or perhaps the patient) by reference to a geographic information system (GIS) database comprising a list of providers and each provider's geographic location (e.g., street address). In some embodiments, the GIS database may be a component of the system database (FIG. 1).

In some embodiments, the set of one or more potential follow-up providers may be further limited to only potential follow-up providers that are (i) above a threshold patient rating and/or (ii) available to perform the follow-up procedure within a threshold timeframe of the date of service determined in block 504.

In embodiments where the system uses a threshold patient rating as a factor for selecting the set of one or more potential follow-up providers, the system can access patient rating data that includes patient ratings of providers and/or patient ratings of procedures performed by providers. For example, one provider may have a generally high patient rating overall, but have low patient ratings for a certain procedure or procedures. Likewise, a provider may have a generally low patient rating overall, but have high patient ratings for a certain procedure or procedures. In operation, the system can use the patient ratings of providers, patient ratings of procedures performed by providers, or some combination of the two as a factor (or factors) to consider when limiting the set of potential follow-up providers to only providers that are above a threshold patient rating. In operation, the system obtains patient ratings of providers and procedures performed by providers from patient feedback or perhaps from other sources. In some embodiments, patient ratings of provider and/or procedures are stored in the system database (FIG. 1) or another data storage system.

In embodiments where the system further limits the set of potential follow-up providers to only potential follow-up providers that are available to perform the follow-up procedure within a threshold timeframe (e.g., up to 10-14 days) from the date of service determined at block 504, the system can access scheduling systems at individual potential follow-up providers to determine which potential follow-up providers have available appointments to perform the follow-up procedure within the threshold timeframe of the date of service. Alternatively, in some embodiments, the system can determine or at least infer whether a particular potential follow-up provider likely has available appointments to perform the follow-up procedure based on an analysis of provider-insurer messages exchanged between insurers and the particular potential follow-up provider that refer to the same follow-up procedure (i.e., include the same procedure identifier).

After determining the set of one or more potential follow-up providers, the system determines, for each potential follow-up provider in the set of one or more potential follow-up providers, the patient's expected out-of-pocket cost to have the potential follow-up provider perform the follow-up procedure. In operation, the system determines the expected out-of-pocket cost for each potential follow-up provider to perform the follow-up procedure in the same way that the system determines the expected out-of-pocket cost for the first provider to perform the procedure, as described with reference to method block 508.

Next, the system selects a follow-up provider (provider$_f$) from the set of one or more potential follow-up providers having the lowest expected out-of-pocket patient cost to perform the follow-up procedure for the patient, or perhaps having an out-of-pocket patient cost that is at least less than some cost threshold. Some embodiments may additionally or alternatively use patient rating to select the follow-up provider (provider$_f$) from the set of one or more potential follow-up providers. For example, if two potential follow-up providers have the same or substantially the same expected out-of-pocket cost for the patient, then the system may, in some embodiments, additionally consider patient rating, and select the provider having the higher patient rating as the follow-up provider.

After the system has selected the follow-up provider at block 538, method 500 advances to method block 540, wherein the system generates and sends the patient (i.e., a client device associated with the patient) one or more messages, wherein the one or more messages (individually or in combination) comprise an identification of (i) the follow-up procedure (procedure$_f$ selected in block 536), (ii) the follow-up provider (provider$_f$ selected in block 538), and (iii) the patient's expected out-of-pocket cost for the selected follow-up provider to perform the follow-up procedure (determined in block 538). In some embodiments, the scheduling engine (FIG. 1) alone or in combination with the recommendation engine (FIG. 1) generates and sends the one or more messages (with the follow-up procedure (procedure$_f$), the follow-up provider (provider$_f$), and the patient's expected out-of-pocket cost for the follow-up provider to perform the follow-up procedure) to the patient's client device.

In response to receiving the message(s) sent from the system to the patient's client device in block 540, the patient's client device displays recommendations based on the one or more messages (or information contained in the messages) within a graphical user interface on the patient's client device (or perhaps associated with the patient's client device). In operation, the recommendations displayed by the patient's client device may be the same as or similar to the example recommendations shown and described with reference to FIG. 4C.

After the system has generated and sent the one or more messages to the patient's client device in method block 540, method 500 advances to method block 542, where the system receives feedback from the patient's client device as to whether the patient wishes to (i) schedule an appointment with the follow-up provider to perform the follow-up procedure or (ii) not schedule an appointment with the follow-up provider to perform the follow-up procedure. In some embodiments, and as described in more detail with reference to the example shown in FIG. 4C, the patient's client device asks the patient whether he/she wishes to schedule the follow-up procedure with the follow-up provider along with a Yes/No prompt. In such embodiments, the client device is configured to (i) inform the system (e.g., via a message or other signaling from the client device to the system) that the patient wishes to schedule the follow-up procedure with the follow-up provider in response to receiving an input from the patient indicating that the patient wishes to schedule the follow-up procedure with the follow-up provider (e.g., the Yes prompt) or (ii) inform the system (e.g., via a message or other signaling from the client device to the system) that the patient does not wish to schedule the follow-up procedure with the follow-up provider in response to receiving an input from the patient indicating the patient does not wish to schedule the follow-up procedure with the follow-up provider (e.g., the No prompt).

At method block 542, if the patient's client device informs the system that the patient wishes to schedule the follow-up procedure with the follow-up provider, then method 500 advances to block 544, where the system sends the patient's client device information for scheduling the follow-up procedure with the follow-up provider, e.g., the phone number (or a link to the phone number) of the follow-up provider, a link to the follow-up provider's web page, a link to the follow-up provider's online scheduling application, and/or other information for the patient's client device to display to the patient for scheduling the follow-up procedure with the follow-up provider. The system later determines whether the patient actually followed through with scheduling the follow-up procedure with the follow-up provider based on the provider-insurer messaging between the follow-up provider and the insurer when the patient schedules the follow-up procedure with follow-up provider. And because the provider-insurer messaging includes a date of service, the system further knows the date when the follow-up provider will perform the follow-up procedure for the patient.

Also at method block 544, after the date that the follow-up provider has performed the follow-up procedure for the patient, the system sends the patient's client device a patient survey (post-procedure$_f$ survey) to obtain patient rating information on the follow-up provider and/or the follow-up procedure performed by the follow-up provider. In some embodiments, block 544 may also include receiving and storing patient's completed survey (or at least the patient rating information contained therein) in the system database (FIG. 1) future reference. After block 544, method 500 ends at method block 548.

But if at method block 542, the patient's client device informs the system that the patient does not wish to schedule the follow-up procedure with the follow-up provider (or if the system receives no further information from the patient's client device regarding the follow-up procedure), then method 500 advances to method block 524, where after the date that the first provider has performed the procedure, the system sends the patient's client device a patient survey to obtain patient rating information on the first provider and/or the procedure performed by the first provider. In some embodiments, block 524 may also include receiving and storing patient's completed survey (or at least the patient rating information contained therein) in the system database (FIG. 1) future reference. After block 524, method 500 ends at method block 548.

In some embodiments, if the patient's client device informs the system that the patient does not wish to schedule the follow-up procedure with the follow-up provider at method block 542, then method 500 returns to block 538, where the system selects another follow-up provider from the set of one or more potential follow-up providers, sets the newly-selected follow-up provider as the follow-up provider (provider$_f$), and then proceeds through method blocks 538-540 as described above with this newly-selected provider as the follow-up provider. In some embodiments, the system may cycle through steps 538-542 with multiple follow-up providers from the set of one or more potential follow-up providers determined at block 538.

Alternatively, in some embodiments, at method block 538, rather than selecting a single follow-up provider from the set of one or more potential follow-up providers, the system may instead select the top 2-5 potential follow-up providers from the set of one or more potential follow-up providers. In some embodiments, the system may select the top 2-5 potential follow-up providers based on expected out-of-pocket cost for the patient, distance from the patient (or the first provider), and/or patient rating.

Then, at method block 540, the system alternatively generates and sends a message (e.g., an email or other type of message) with (i) a list of the top 2-5 potential follow-up providers, (ii) the corresponding expected out-of-pocket cost for each of the top 2-5 potential follow-up providers, and (iii) contact information (e.g., phone number, webpage, link to scheduling system (if applicable), or other contact information) for the patient to use in scheduling the follow-up procedure with the top 2-5 potential follow-up providers. In some embodiments, the message may additionally include patient ratings for each of the top 2-5 potential follow-up providers. In such embodiments, the system can later determine whether the patient scheduled an appointment to have one of the top 2-5 potential follow-up perform the follow-up procedure, and after the date of the follow-up procedure, send a patient survey to the patient's client device, similar to method block 544.

EXAMPLE USE CASES

Example 1: If the appointment is for the current day based on the date of service in the 270 request and/or 271 response, then the system (e.g., system 102 in FIG. 1) may send a message(s) to the patient's client device (e.g., client device 128) later in the day or evening after the appointment to solicit patient rating information regarding the provider and/or the procedure (e.g., by having the patient fill out a review of the facility, the procedure, and/or the provider). The system can then store the patient rating information in the system database (e.g., system database 108) for future reference.

Example 2: If the appointment is at an emergency room for the current day (determined based at least in part on the provider identifier in the 270 request and/or 271 response), then system (e.g., system 102 in FIG. 1) may send a message(s) to the patient's client device (e.g., client device 128) in the evening or perhaps the next day to prompt the patient to follow up with his or primary care physician (PCP). In some embodiments, the message(s) may include the patient's PCP's contact information if available. Also, in some embodiments, the system may additionally notify (e.g., via email, text, letter, phone call/automated voice response, etc.) the patient's PCP of the patient's emergency room visit. Additionally, in some embodiments, the system may also generate an HL7 record (or similar record or message) to update the patient's electronic medical records (EMR) with the patient's PCP, insurance company, and/or third-party patient EMR repository.

Example 3: If the appointment is scheduled for one or more days in the future, then the system (e.g., system 102 in FIG. 1) sends a message(s) that includes a variety of information depending at least in part on the Service Type Code (STC) in the 270/271 (or similar) messaging and/or perhaps additional information.

For example, if the procedure identifier in the 270/271 messaging is for a Diagnostic Radiology service, then the system will send a message(s) including, for example, (i) the patient's year to date deductible status, (ii) coinsurance or copayment to enable patient to estimate out of pocket expense, and/or (iii) an indication of the patient's estimated out of pocket expense. The message(s) may also include suggestions on alternative facilities with lower cost estimates, or provide click-through access to tools and/or websites wherein the patient can locate lower cost and/or higher quality providers. Additionally or alternatively, if the provider scheduled to perform the procedure is outside of the patient's insurance network/plan, then the message may include information such as (i) an alert that the scheduled provider is out of the patient's insurance network/plan, (ii) an indication as to what portion of the cost (if any) that the patient's insurance company will pay to the out-of-network provider to perform the scheduled procedure for the patient, (iii) an indication of the patient's estimated out-of-pocket expense to have the scheduled provider perform the scheduled procedure, (iv) an indication of one or more alternative in-network providers offering the scheduled procedure that the patient may wish to consider instead of the scheduled provider, and/or (v) a comparison showing the difference between the patient's expected out-of-pocket cost to have the schedule procedure performed by the scheduled provider versus the patient's expected out-of-pocket expense to have the scheduled performed by one or more of the alternative in-network providers.

Example 4: Regardless of when the appointment is scheduled to occur, and in addition to any of the above-described information, the system (e.g., system 102 in FIG. 1) may send a message that includes information for preparing for the scheduled procedure (e.g., an office visit with a specialist), questions to ask (or information to provide to) the scheduled provider (e.g., questions about potential follow-up procedures and follow-up providers from which to obtain the potential follow-up procedures.), and/or similar information relating to the scheduled procedure (office visit).

Additionally, in some embodiments, the system (e.g., system 102 in FIG. 1) may determine whether the patient has a Health Savings Account (HSA) or Health Reimbursement Account (HRA) based on the patient data, and if so, the system may send a message to the patient's client device with information regarding (i) whether the scheduled procedure is eligible for payment with funds from the patient's HSA/HRA account, (ii) whether the patient's HSA/HRA account has sufficient funds to pay the expected out-of-pocket expense for the scheduled procedure, (iii) if applicable, a suggestion that the patient deposit additional funds into the HSA/HRA account to pay for the expected out-of-pocket expense for the scheduled procedure, and/or (iv) if the patient does not have an HSA/HRA account, an estimate of how much the patient would save if the patient were to use HSA/HRA funds to pay for the expected out-of-pocket expense for the scheduled procedure.

In some embodiments, if the STC type code is 02 (indicating an ambulance) for the current day, then the computing system may alert the patient's PCP. The patient's PCP may be available from a past repository of claims and physician attribution algorithms, or it may be available from the patient's own indication/selection of PCP when the patient enrolled in his/her insurance plan and/or when the patient signed up to use the system (e.g., system 102 in FIG. 1) to receive healthcare recommendation messages as described herein.

Additionally, in some embodiments, the system (alone or in combination with an application or other software running on the patient's smartphone or tablet) may enable a patient to self-schedule a text prompt, app notification, or similar reminder associated with the appointment. In some embodiments, the reminder may correspond to or include an ICS (or similar) calendar file to add the appointment into the patient's calendar and/or an email or text invitation suitable for use with any electronic calendaring system. Similarly, the reminder may correspond to a phone call reminder for the appointment.

Example 5: In another example, a patient makes an appointment for an MRI/CT Scan (a procedure) with a first provider. Shortly after the patient schedules the appointment with the first provider to perform the MRI/CT Scan procedure, the first provider sends a request message (e.g., a 270 request) to the patient's insurer asking whether and (and perhaps the extent to which) the insurer will cover the first provider performing the MRI/CT scan on some future service date (e.g., a week from the message date). And in response to the receiving the request message from the first provider, the patient's insurer sends a response (e.g., a 271 response) to the first provider indicating, for example, whether the patient is covered by the insurer, whether the MRI/CT Scan is covered by the patient's insurance plan, etc. The first provider and the insurer may exchange other messages associated with the patient's scheduled appointment for the MRI/CT Scan as well.

Based on the provider-insurer messaging, the system (e.g., system 102 in FIG. 1) determines (i) an expected patient out-of-pocket cost for the first provider to perform the MRI/CT Scan and (ii) a second provider that is (a) located within a threshold geographic distance (e.g., within 10 miles) of the first provider and (b) has an expected patient out-of-pocket cost to perform the MRI/CT Scan that is less than the expected patient out-of-pocket cost for the first provider to perform the MRI/CT Scan. Then, the system sends one or more messages to the patient's computing device (e.g., client device 128 in FIG. 1), where the one or more messages include (i) an identification of the first provider, (ii) the expected patient out-of-pocket cost for the first provider to perform the MRI/CT Scan, (iii) an identification of the second provider, and (iv) the expected patient out-of-pocket-cost for the second provider to perform the MRI/CT Scan.

In response to receiving the one or more messages from the system, the patient's client device then displays a comparison of the expected patient-out-of-pocket costs for the first provider (that the patient originally made the appointment with) and the second provider (that the system selected as sufficiently close to the first provider and able to perform the MRI/CT Scan at the lower cost). In some embodiments, the recommendation may take the form of the recommendations shown and described with reference to FIG. 4A for example.

Example 6: In another example, a patient makes an appointment for an MRI/CT Scan (a medical procedure) with a first provider. Shortly after the patient schedules the appointment with the first provider to perform the MRI/CT Scan procedure, the first provider sends a request message (e.g., a 270 request) to the patient's insurer asking whether and (and perhaps the extent to which) the insurer will cover the first provider performing the MRI/CT scan that day (i.e., the same day as the message date). And in response to the receiving the request message from the first provider, the patient's insurer sends a response (e.g., a 271 response) to the first provider indicating, for example, whether the patient is covered by the insurer, whether the MRI/CT Scan is covered by the patient's insurance plan, etc. The first provider and the insurer may exchange other messages associated with the patient's scheduled appointment for the MRI/CT Scan as well.

The system (e.g., system 102 in FIG. 1) determines an expected patient out-of-pocket cost for the first provider to perform the MRI/CT Scan later that day. Next, the system (i) sends one or more messages to the patient's computing device (e.g., client device 128 in FIG. 1), where the one or more messages include the expected patient out-of-pocket cost for the first provider to perform the MRI/CT Scan, and (ii) schedules a follow-up survey for later that day or the following day to have the patient rate his or her experience with having the first provider perform the MRI/CT Scan.

When the time for the scheduled follow-up survey arrives, the system sends the follow-up survey to the patient's computing device. If the patient responds to the survey with a rating of his or her experience with having the first provider perform the MRI/CT Scan, then the recommendation engine determines (i) a second provider that is (a) located within a threshold geographic distance (e.g., within 10 miles) of the first provider and (b) has an expected patient out-of-pocket cost to perform the MRI/CT Scan that is less than the expected (or perhaps actual) patient out-of-pocket cost for the first provider to perform the MRI/CT Scan. The system then sends one or more messages to the patient's computing device, where the one or more messages comprise (i) an identification of the second provider, and (ii) the expected patient out-of-pocket-cost for the second provider to perform the MRI/CT Scan. In operation, the patient's computing device may save the one or more messages for future reference by the patient in case the patient needs to have the procedure performed again in the future.

Example 7: In another example, a patient arrives at the emergency room. The emergency room (i.e., the first provider) sends a request message (e.g., a 270 request) to the patient's insurer asking whether and (and perhaps the extent to which) the insurer will cover the first provider treating the patient in the emergency room that day (i.e., the same day as the 270 message date). In some embodiments, the 270 message may also indicate the type of treatment that the emergency room expects to provider, e.g., based on the injury for which the emergency room will treat the patient. In response to the receiving the request message from the first provider (i.e., the emergency room), the patient's insurer sends a response (e.g., a 271 response) to the first provider indicating, for example, whether the patient is covered by the insurer, whether the emergency room visit (and perhaps the expected type of treatment) is covered by the patient's insurance plan, etc. The first provider and the insurer may exchange other messages associated with the patient's emergency room visit as well.

The system (e.g., system 102 in FIG. 1) determines an expected patient out-of-pocket cost for the emergency room to treat the patient that day. Next, the system (i) sends one or more messages to the patient's computing device (e.g., client device 128 in FIG. 1), where the one or more messages include (i) the expected patient out-of-pocket cost for the emergency room to treat the patient, and (ii) one or more nearby alternative urgent care facilities that are currently open (based on the provider data) and have a lower expected out-of-pocket cost for the patient. With this information, and if the patient is able, the patient may simply leave the emergency room and go to the nearby urgent care facility to be treated at a lower cost (and perhaps more quickly than) receiving treatment at the emergency room.

Example 8: In another example, a patient makes an appointment for an office visit (the procedure) with an orthopedic specialist (the provider) and the date of service is either today or sometime in the future. Shortly after the patient schedules the appointment with the provider (the orthopedic specialist) for the procedure (the office visit), the provider sends a request message (e.g., a 270 request) to the patient's insurer asking whether and (and perhaps the extent to which) the insurer will cover the office visit with the orthopedic specialist on the date of service. And in response to the receiving the request message from the provider, the patient's insurer sends a response (e.g., a 271 response) to the provider indicating, for example, whether the patient is covered by the insurer, whether the office visit with the orthopedic specialist is covered by the patient's insurance plan, etc. The provider and the insurer may exchange other messages associated with the patient's scheduled office visit with the orthopedic specialist as well.

The system (e.g., system 102 in FIG. 1) determines the most likely follow-up procedure that the orthopedic special is likely to prescribe based at least in part on the patient data and the provider data. The patient data includes any of (i) patient demographic data (e.g., age, gender, ethnicity, national origin, occupation, education, income, address, family status, and/or other demographic data), and/or (ii) patient health data (e.g., known diseases, allergies, current medications, past medications, doctor visit history, family history of disease, prior injuries/treatments, and/or other health data). The provider data includes the provider's specialty, the follow-up procedures that the provider has prescribed in the past, and/or other data about the first provider.

In this example, the system (e.g., system 102 in FIG. 1) predicts that the orthopedic specialist will probably recommend that the patient have an MRI based on the patient data (e.g., the patient is known to have osteoporosis and has visited this specialist before) and the provider data (e.g., this orthopedic specialist tends to prescribe MRIs for his or her patients, or at least for the patients with osteoporosis). Based on this predicted follow-up procedure (i.e., the MRI), the system will send the patient's client device (e.g., client device 128) one or more messages that include (i) the predicted follow-up procedure (the MRI), (ii) at least one nearby follow-up provider (e.g., a clinic that performs MRIs), and (iii) the expected patient out-of-pocket cost to have the proposed follow-up provider (the nearby clinic) perform the predicted follow-up procedure (the MRI). In response to receiving the message(s) from the system, the patient's client device displays the recommended clinic for performing the MRI. In some embodiments, the recommendation may take the form of the recommendations shown and described with reference to FIG. 4C for example.

With information regarding the recommended clinic and expected out-of-pocket costs, the patient can consult with the orthopedic specialist about the clinic during the office visit if the orthopedic specialist recommends an MRI.

Example 9: In yet another example, the patient goes to the pharmacy (the provider) to fill a prescription. In connection with filling the prescription, the pharmacy (the provider) sends a request message (e.g., a 270 request or similar) to the patient's insurer asking whether and (and perhaps the extent to which) the insurer will cover the prescription. The request message from the pharmacy specifies (e.g., via a service type field in the request message) that the prescription is "B3 Brand Name Prescription Drug—Non Formulary" (thus, the procedure is "fill B3 Brand Name Prescription Drug—Non Formulary"). In response to the receiving the request message from the pharmacy, the patient's insurer sends a response (e.g., a 271 response) to the pharmacy indicating, for example, whether the patient is covered by the insurer, whether the filling the prescription is covered by the patient's insurance plan, etc. The pharmacy and the insurer may exchange other messages associated with filling the patient's prescription as well.

Based on the provider-insurer messaging, the system (e.g., system 102 in FIG. 1) (i) determines that the provider (the pharmacy) is "in-network" based on the provider code, (ii) determines the expected out-of-pocket cost for the provider (the pharmacy) to perform the procedure (fill the B3 Brand Name Prescription Drug—Non Formulary) and (i) sends one or more messages to the patient's client device (e.g., client device 128 in FIG. 1) with names of generic substitutes so that the patient can ask the pharmacist about the generic drug.

Example 10: In a final example, the patient goes to an out-of-network pharmacy (the first provider) to fill a prescription. In connection with filling the prescription, the out-of-network pharmacy (the first provider) sends a request message (e.g., a 270 request or similar) to the patient's insurer asking whether and (and perhaps the extent to which) the insurer will cover the prescription. The request message from the out-of-network pharmacy specifies (e.g., via a service type field in the request message) that the prescription is "B3 Brand Name Prescription Drug—Non Formulary" (thus, the procedure is "fill B3 Brand Name Prescription Drug—Non Formulary"). In response to the receiving the request message from the out-of-network pharmacy, the patient's insurer sends a response (e.g., a 271 response) to the out-of-network pharmacy indicating, for example, whether the patient is covered by the insurer, whether the filling the prescription is covered by the patient's insurance plan, etc. The out-of-network pharmacy and the insurer may exchange other messages associated with filling the patient's prescription as well.

Based on the provider-insurer messaging, the system (e.g., system 102 in FIG. 1) determines that the pharmacy is "out-of-network" based on the provider code, (ii) determines the expected patient out-of-pocket cost for the out-of-network pharmacy (the first provider) to fill the B3 Brand Name Prescription Drug—Non Formulary prescription (perform the procedure) for the patient, (iii) selects an "in-network" pharmacy (a second provider) that is geographically close to the out-of-network pharmacy (the first provider), (iv) determines the expected patient out-of-pocket cost to have the in-network pharmacy (the second provider) fill the particular prescription (perform the procedure), and (v) sends one or more messages to the patient's client device (e.g., client device 128 in FIG. 1) with a recommendation that the patient have the prescription filled at the nearby in-network pharmacy.

For example, the one or more messages that the system sends to the patient's client device may include (i) an identification of the out of network pharmacy (the first provider), (ii) the expected out-of-pocket cost to have the out-of-network pharmacy (the first provider) fill the prescription (perform the procedure), (iii) an identification of the in-network pharmacy (the second provider), and (iv) the expected out-of-pocket cost for the in-network pharmacy (the second provider) to fill the prescription (perform the procedure) for the patient. In some embodiments, the recommendation may take the form of the recommendations shown and described with reference to FIG. 4A for example.

While particular aspects and embodiments are disclosed herein, other aspects and embodiments will be apparent to those skilled in the art in view of the foregoing teaching. For example, while the embodiments are described with respect to applications for text-based news stories, the disclosed systems and methods are not so limited. The various aspects and embodiments disclosed herein are for illustration purposes only and are not intended to be limiting, with the true scope and spirit being indicated by the following claims.

What is claimed is:

1. A method comprising:
obtaining, by a collector over a secure electronic communication link, one or more encrypted provider-insurer eligibility messages sent between a provider and an insurer for verifying patient insurance eligibility, wherein the one or more encrypted provider-insurer eligibility messages comprise (i) a patient identifier, (ii) a provider identifier, and (iii) a date of service, wherein the collector includes one or more processors and one or more electronic communication interfaces;
decrypting, by the collector, the one or more encrypted provider-insurer eligibility messages;
determining a first medical procedure, a first provider, and a date of service based on the decrypted one or more encrypted provider-insurer eligibility messages;
generating, by a recommendation engine, an expected patient cost for the first provider to perform the first medical procedure for a patient associated with the patient identifier, wherein the recommendation engine includes one or more processors and one or more electronic communication interfaces;
determining, by the recommendation engine, a set of one or more alternative providers, wherein each alternative provider is located within a threshold geographic distance from the first provider;
for each alternative provider in the set of one or more alternative providers, generating, by the recommendation engine, an expected patient cost for the alternative provider to perform the first medical procedure for the patient associated with the patient identifier;
selecting, by the recommendation engine, a second provider from the set of one or more alternative providers, wherein selecting the second provider comprises selecting a second provider having an expected patient cost that is less than the expected patient cost for the first provider, and that is available to perform the first medical procedure for the patient within a threshold timeframe of the determined date of service;
predicting, via a Multinomial Logistic Regression analysis, a follow-up medical procedure, related to but different from the first medical procedure based at least in part on the first medical procedure, patient medical history, and a history of procedures recommended by the first provider, wherein the Multinomial Logistic Regression analysis receives as input a plurality of medical procedures, patient data associated with the patient, and provider data associated with the first provider that is indicative of past procedures prescribed by the first provider, and outputs a set of probabilities associated with a plurality of follow-up medical procedures, wherein the predicted follow-up medical procedure correspond to a follow-up medical procedure of the plurality of follow-up medical procedures associated with a probability that exceeds a threshold probability;
determining a follow-up provider to perform the predicted follow-up procedure;
generating, by a scheduling engine, one or more messages comprising (i) the first provider, (ii) the expected patient cost for the first provider to perform the first medical procedure, (iii) the second provider, (iv) the expected patient cost for the second provider to perform the medical procedure, and (v) information identifying the predicted follow-up medical procedure and the determined follow-up provider, wherein the scheduling engine includes one or more processors and one or more communication interfaces;
prior to the date of service, sending, by the scheduling engine via one or more networks, the one or more messages to a client device associated with the patient.

2. The method of claim 1, further comprising:
in response to receiving the request to schedule the first medical procedure with the second provider, sending, to the client device, information that facilitates scheduling the first medical procedure with the second provider.

3. The method of claim 1, wherein selecting a second provider from the set of one or more alternative providers further comprises selecting a second provider having a patient rating that is at least as high as a patient rating of the first provider.

4. The method of claim 1, further comprising:
receiving, from the client device, a request to not schedule the first medical procedure with the second provider; and
in response to receiving the request to not schedule the first medical procedure with the second provider, selecting a third provider from the set of one or more alternative providers, wherein selecting the third provider comprises selecting a third provider from the set that has at least one of (i) an expected patient cost to perform the first medical procedure that is less than the expected patient cost for the first provider to perform the first medical procedure or (ii) a patient rating that is higher than a patient rating for the first provider.

5. The method of claim 1, wherein the encrypted one or more provider-insurer eligibility messages comprises one or more of a 270 request, a 271 response, a 278 request, or a 278 response.

6. The method of claim 1, wherein generating an expected patient cost for the first provider to perform the first medical procedure for the patient associated with the patient identifier comprises:
accessing a system database comprising billing records of the first medical procedure performed by the first provider; and
generating an expected patient cost for the first provider to perform the first medical procedure based on one or more of (i) whether the insurer covers the first medical procedure, (ii) billing history between the first provider and the insurer for the first medical procedure, (iii) whether the first provider and the insurer have an agreed-upon price to perform the first medical procedure, and/or (iv) whether the first provider participates in an insurance plan that the patient has purchased from the insurer.

7. The method of claim 1, wherein generating an expected patient cost for the first provider to perform the first medical procedure for the patient associated with the patient identifier comprises:
generating a claim request message identifying the patient, the first provider and the first medical procedure;
sending the generated claim request message to the insurer;

in response to sending the generated claim request message to the insurer, receiving a claim response message from the insurer, wherein the claim response message comprises one of (i) expected cost for the first provider to perform the procedure for the patient or (ii) information for calculating the expected cost for the first provider to perform the procedure for the patient.

8. The method of claim 1, wherein the one or more messages comprising the first provider, the expected patient cost for the first provider to perform the first medical procedure, the second provider, and the expected patient cost for the second provider to perform the first medical procedure comprises a single message displaying a comparison of the expected patient cost for the first provider to perform the first medical procedure and the expected patient cost for the second provider to perform the first medical procedure.

9. A system comprising:
a plurality of collector appliances, wherein each collector appliance is configured to obtain one or more provider-insurer eligibility messages from one of an insurer or a gateway positioned between a provider and the insurer, wherein the one or more provider-insurer eligibility messages comprise a patient identifier, a provider identifier, and a date of service;
a collector configured to receive, over a secure electronic communication link, one or more encrypted provider-insurer eligibility messages from one or more of the plurality of collector appliances and to decrypt the provider-insurer eligibility messages, wherein the collector includes one or more processors and one or more electronic communication interfaces;
a recommendation engine configured to receive obtained decrypted provider-insurer eligibility messages from the collector, and for an individual set of one or more obtained messages, (i) determine a medical procedure, a first provider, and a date of service based on the set of one or more obtained messages, (ii) generate an expected patient cost for the first provider to perform the medical procedure for the patient associated with the patient identifier, (iii) determine a set of one or more alternative providers, wherein each alternative provider is located within a threshold geographic distance of the first provider, (iv) for each alternative provider in the set of one or more alternative providers, generate an expected patient cost for the alternative provider to perform the medical procedure for the patient, and (v) select a second provider from the set of one or more alternative providers, wherein the selected second provider has an expected patient cost that is less than the expected patient cost for the first provider, and is available to perform the medical procedure for the patient within a threshold timeframe of the determined date of service, wherein the recommendation engine includes one or more processors and one or more electronic communication interfaces; and
a scheduling engine configured to (i) generate one or more messages comprising the first provider, the expected patient cost for the first provider to perform the medical procedure, the second provider, the expected patient cost for the second provider to perform the medical procedure, and a control that facilitates scheduling the second provider for performing the medical procedure, (ii) prior to the date of service, send the one or more messages via one or more networks to a client device associated with the patient, wherein the scheduling engine includes one or more processors and one or more communication interfaces, thereby reducing client device processor time and network bandwidth usage that would have been required for the client device to individually identify alternative providers and solicit expected patient costs from each alternative provider separately via the one or more networks, and (iii) subsequently receive, in response to selection of the control of the message, a request to schedule the medical procedure with the second provider,
wherein the recommendation engine is further configured to (i) predict, via a Multinomial Logistic Regression analysis, a follow-up procedure based at least in part on the patient identifier, patient medical history, and a history of procedures recommended by the first provider, and (ii) determine a follow-up provider to perform the predicted follow-up procedure for the patient, wherein the Multinomial Logistic Regression analysis receives as input a plurality of medical procedures, patient data associated with the patient, and provider data associated with the first provider that is indicative of past procedures prescribed by the first provider, and outputs a set of probabilities associated with a plurality of follow-up medical procedures, wherein the predicted follow-up medical procedure correspond to a follow-up medical procedure of the plurality of follow-up medical procedures associated with a probability that exceeds a threshold probability; and
wherein the scheduling engine is further configured to send information identifying the predicted follow-up procedure and the determined follow-up provider to a client device associated with the patient.

10. The system of claim 9, wherein in response to receiving the request, the scheduling engine is further configured to send, to the client device, information that facilitates scheduling the medical procedure with the second provider.

11. The system of claim 9, wherein the selected second provider further has a patient rating that is at least as high as a patient rating of the first provider.

12. The system of claim 9:
wherein the scheduling engine is further configured to receive, from the client device, a request to not schedule the medical procedure with the second provider, and
wherein the recommendation engine is further configured to, in response to the scheduling engine receiving the request not to schedule the medical procedure with the second provider, select a third provider from the set of one or more alternative providers, wherein the selected third provider has at least one of (i) an expected patient cost to perform the medical procedure that is less than the expected patient cost for the first provider to perform the medical procedure or (ii) a patient rating that is higher than a patient rating for the first provider.

13. The system of claim 9, wherein the set of one or more provider-insurer eligibility messages comprises one or more of a 270 request, a 271 response, a 278 request, or a 278 response.

14. The system of claim 9, further comprising:
a system database comprising billing records of the medical procedure performed by the first provider; and
wherein the recommendation engine is configured to generate the expected patient cost for the first provider to perform the medical procedure based on one or more of (i) whether the insurer covers the medical procedure, (ii) billing history between the first provider and the insurer for the medical procedure, (iii) whether the first provider and the insurer have an agreed-upon price to perform the medical procedure, and/or (iv) whether the first provider participates in an insurance plan that the patient has purchased from the insurer.

15. The system of claim 9, wherein the recommendation engine is further configured to generate an expected patient cost for the first provider to perform the medical procedure for the patient associated with the patient identifier by (i) generating a claim request message identifying the patient, the first provider and the medical procedure; (ii) sending the generated claim request message to the insurer; and (iii) in response to sending the generated claim request message to the insurer, receive a claim response message from the insurer, wherein the claim response message comprises one of (a) expected cost for the first provider to perform the procedure for the patient or (b) information for calculating the expected cost for the first provider to perform the procedure for the patient.

16. The system of claim 9,
wherein the scheduling engine is further configured to send information identifying the predicted follow-up procedure and the determined follow-up provider to a client device associated with the patient.

17. The system of claim 9, wherein the one or more messages comprising the first provider, the expected patient cost for the first provider to perform the medical procedure, the second provider, and the expected patient cost for the second provider to perform the medical procedure comprises a single message displaying a comparison of the expected patient cost for the first provider to perform the medical procedure and the expected patient cost for the second provider to perform the medical procedure.

* * * * *